United States Patent
Binder et al.

(10) Patent No.: US 12,042,383 B2
(45) Date of Patent: Jul. 23, 2024

(54) MANDIBULAR AUGMENTATION IMPLANTS, METHODS, AND USES

(71) Applicant: Webco Partners, LLC, Beverly Hills, CA (US)

(72) Inventors: William J. Binder, Pacific Palisades, CA (US); Edward Leicht, Oak View, CA (US)

(73) Assignee: Webco Partners, LLC, Beverly Hills, CA (US)

( * ) Notice: Subject to any disclaimer, the term of this patent is extended or adjusted under 35 U.S.C. 154(b) by 0 days.

(21) Appl. No.: 18/320,988

(22) Filed: May 21, 2023

(65) Prior Publication Data

US 2023/0285152 A1 Sep. 14, 2023

Related U.S. Application Data

(62) Division of application No. 17/494,694, filed on Oct. 5, 2021.

(60) Provisional application No. 63/087,801, filed on Oct. 5, 2020.

(51) Int. Cl.
*A61F 2/28* (2006.01)
*A61F 2/00* (2006.01)

(52) U.S. Cl.
CPC .......... *A61F 2/2803* (2013.01); *A61F 2/0059* (2013.01); *A61F 2002/2807* (2013.01)

(58) Field of Classification Search
CPC .......... A61F 2/2803; A61F 2/0059; A61F 2002/2807
See application file for complete search history.

(56) References Cited

U.S. PATENT DOCUMENTS

| | | | |
|---|---|---|---|
| 4,790,849 A | 12/1988 | Terino | |
| 4,969,901 A | 11/1990 | Binder | |
| 4,990,160 A * | 2/1991 | Terino | A61F 2/2803 D24/155 |
| 6,277,150 B1 | 8/2001 | Crawley et al. | |
| 7,396,232 B2 | 7/2008 | Fromovich et al. | |
| 9,056,017 B2 | 6/2015 | Kotlus | |
| 9,114,013 B2 | 8/2015 | Jordan et al. | |
| 9,265,650 B2 | 2/2016 | Hegde et al. | |
| 10,052,186 B2 | 8/2018 | Papay et al. | |
| 10,327,870 B2 | 6/2019 | Lee | |
| 2007/0067041 A1 | 3/2007 | Kotoske | |

(Continued)

FOREIGN PATENT DOCUMENTS

WO 2018172982 A1 9/2018

OTHER PUBLICATIONS

Alghoul, et al., Retaining Ligaments of the Face: Review of Anatomy and Clinical Applications, Aesth. Surg. J. 33(6): 769-782 (2013).

(Continued)

*Primary Examiner* — Dinah Baria
(74) *Attorney, Agent, or Firm* — UltimatEdge IP Law Group, P.C.; Dean G. Stathakis

(57) ABSTRACT

The present specification discloses a method of augmenting or enhancing a chin of an individual comprising excising the left and right anterior mental fibrous condensation anteriorly and elevating the left and right medial mandibular and mandibulocutaneous ligaments to create an extended subperiosteal pocket as well as mandibular implants designed to be implanted using such methods.

20 Claims, 20 Drawing Sheets

(56) References Cited

U.S. PATENT DOCUMENTS

2014/0052264 A1   2/2014  Hufen et al.
2018/0110593 A1   4/2018  Khalil
2018/0344894 A1*  12/2018 Kay .................. A61B 17/32
2020/0205984 A1   7/2020  Lee et al.

OTHER PUBLICATIONS

WIPO, PCT ISA 210 International Search Report for IA Patent Application Serial No. PCT/US2021/053637, pp. 5 (Feb. 11, 2022).
WIPO, PCT ISA 237 Written Opinion for IA Patent Application Serial No. PCT/US2021/053637, pp. 9 (Feb. 11, 2022).
WIPO, PCT IPEA 409 International Preliminary Report on Patentability for IA Patent Application Serial No. PCT/US2021/053637, pp. 32 Jun. 1, 2023).

* cited by examiner

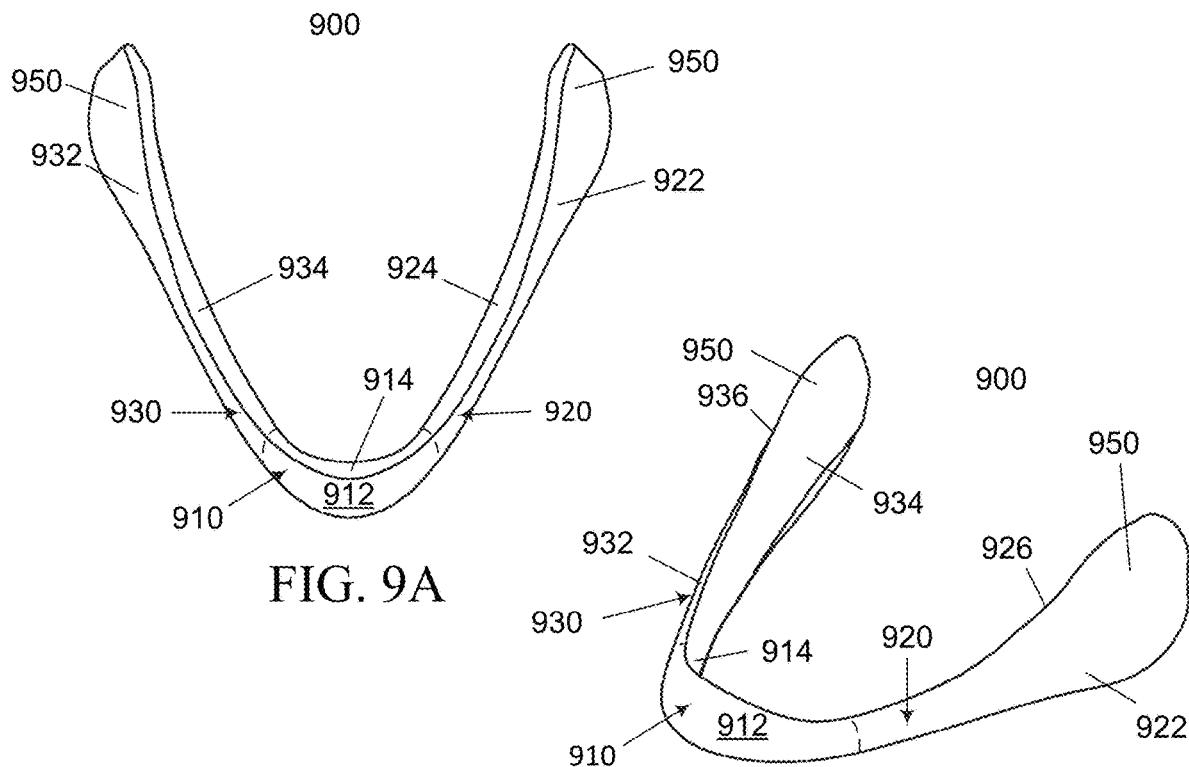
FIG. 9A
FIG. 9B
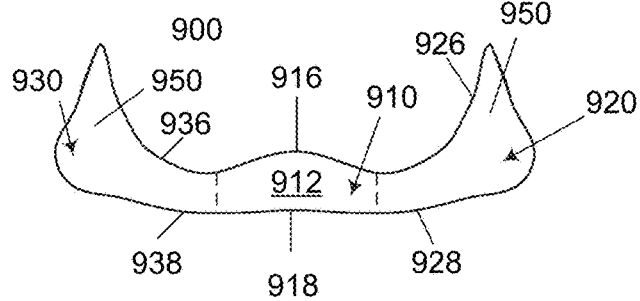
FIG. 9C
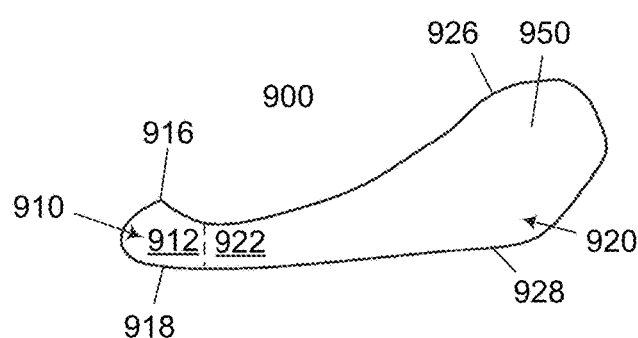
FIG. 9D

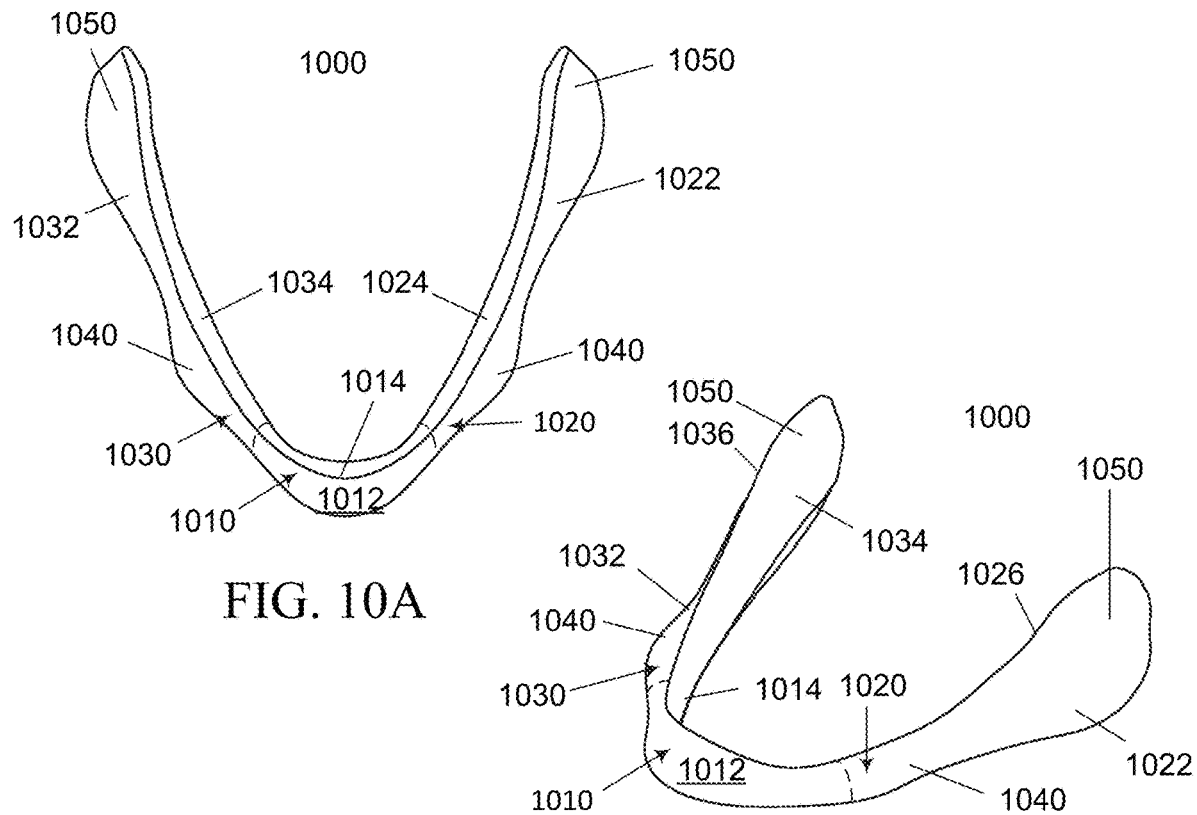
FIG. 10A
FIG. 10B
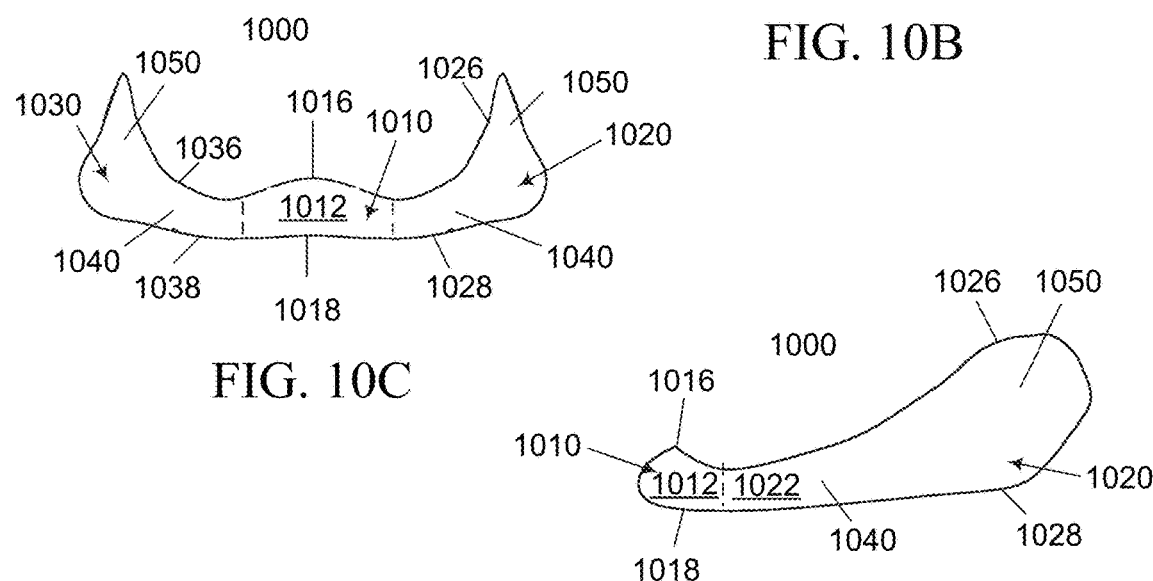
FIG. 10C
FIG. 10D

MANDIBULAR AUGMENTATION IMPLANTS, METHODS, AND USES

This application is a divisional that claims the benefit of priority and is entitled to the filing date pursuant to 35 U.S.C. § 121 of U.S. Non-Provisional patent application Ser. No. 17/494,694, filed Oct. 5, 2021, a 35 U.S.C. § 111 patent application which claims the benefit of priority and is entitled to the filing date pursuant to 35 U.S.C. § 119(e) of U.S. Provisional Patent Application 63/087,801, filed Oct. 5, 2020, the content of each of which is hereby incorporated by reference in its entirety.

BACKGROUND

The invention relates, in some aspects, to mandibular augmentation implants and methods of implantation.

The chin is an important and prominent region of the lower face. For example, a well-defined jawline structure is the cornerstone of a balanced attractive face, male or female. As such, many individuals are bothered by a recessed or "weak" chin as it detracts from their facial appearance. A recessed chin can produce facial features which lack aesthetically pleasing proportion including, e.g., creating a full or "double" chin, making a perfectly sized nose appear too large, or making the neck look "fleshy".

Mandibular augmentation or enhancement surgery, also called mentoplasty, can correct a weak or recessed chin by strengthening the appearance of a receding chin, providing proportion to the chin, improving the contours of neck and jawline, and/or restoring an overall balance to the appearance and profile of an individual's face. Typically, surgery involves placement of an implant around a patient's existing jawline to augment the size and shape of the chin and achieve a more naturally attractive balance between facial features.

However, the anatomical features of the chin have limited the effectiveness of current surgical procedures for mandibular augmentation or enhancement. For example, retaining ligaments of the mandible prevent the extent to which a chin implant can be positioned, thereby constraining the size of a chin implant, and limiting the region a chin implant can be placed. These size and placement limitations place restrictions to the extent a chin and be augmented or enhanced. Therefore, there is a need for improved surgical procedures for mandibular augmentation or enhancement. The present specification discloses such improved surgical procedures as well as novel chin implants that can now be advantageously used because of these improved surgical procedures for mandibular augmentation or enhancement.

SUMMARY

Aspects of the present specification disclose a mandibular implant comprising a body having a substantially U-shaped structure comprising a first end region and a second end region, the body sized and dimensioned to an axial length configured to extend from a point laying in a region between an attachment location of a left mandibular osteocutaneous ligament and a left gonial angle to a region between the attachment location of the right mandibular osteocutaneous ligament and the right gonial angle. The disclosed mandibular implant can have an axial length that extends past the attachment location of the left mandibular osteocutaneous ligament by about 3 mm to about 5 cm and extends past the attachment location of the right mandibular osteocutaneous ligament by about 3 mm to about 5 cm, and can have an axial length that extends to the left gonial angle and to the right gonial angle. The mandibular implant of claim 1, wherein a body of a mandibular implant disclosed herein can comprise a mental arch, a left lateral arm, and a right lateral arm and can further comprise a ramus extension projecting superiorly from a top edge of the first end region of the body or left lateral arm and/or a ramus extension projecting superiorly from a top edge of the second end region of the body or right lateral arm. In addition, a body of a mandibular implant disclosed herein can further comprise one or more protrusions projecting radially outward from an outer surface of the body, and/or one or more tabs projecting posteriorly from an inner surface of the body, such tabs comprising a base tab, a submental tab, an extended tab, or any combination thereof. The disclosed body has an outer surface and an inner surface each or which can be smooth or textured. The disclosed body is composed of implantable biomaterial and can be flexible and can have a unitary structure or comprise an outer shell and an inner core, with the shell being one unitary layer or a plurality of layers. The disclosed body can also be configured with a hole interior space that can be substantially filled with a filler.

Other aspects of the present specification disclose a method of mandibular augmentation or enhancement. The disclosed methods comprises accessing one or more segments of a left and/or a right anterior mental fibrous condensation; releasing one or more segments of the left and/or the right anterior mental fibrous condensation from their one or more respective mandibular attachment sites; subperiosteally releasing one or more mandibular ligaments from their respective one or more mandibular attachment points to form a subperiosteal implantation cavity; and inserting of a mandibular implant into the subperiosteal implantation cavity. A method disclosed herein can create a subperiosteal implantation cavity that extended laterally any distance past an attachment site of the one or more mandibular ligaments such as a mandibulocutaneous ligament. After insertion the mandibular implant using a method disclosed herein, the implant acts as a spacer to maintain periosteum above the mandible and inhibit periosteal re-attachment and can augment a jaw area by a volume that is at least about 20% more than the volume of the mandibular implant. A method disclosed herein provides for the inserted mandibular implant to augment a jaw area from a point posterior to the location of an attachment site of a left mandibulocutaneous ligament to a point posterior to the location an attachment site of a right mandibulocutaneous ligament. A method disclosed herein can lift, reduces or eliminates jowls and be performed with or without a concomitant face lift procedure and/or a dermal filler procedure. Other aspects of the present specification disclose a mandibular implant disclosed herein for use in the augmentation or enhancement of a jaw of an individual. Other aspects of the present specification disclose a use of a mandibular implant disclosed herein in the augmentation or enhancement of a jaw of an individual.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIG. 1B showing an oblique left lateral view; and FIG. 1C showing a posterior view;

FIG. 2B showing three false ligaments of the face;

FIG. 3B showing the positions of the left anterior mental fibrous condensation, the left medial mandibular ligament, and the left mandibulocutaneous ligament;

FIG. 4B illustrating the continuing incision with one hand while locating and protecting the mental nerve with the other, and the excision of the anterior mental fibrous condensation segments; FIG. 4C illustrating the direction and location of the subperiosteal implant cavity to be created using a subperiosteal elevator; FIG. 4D illustrating creating a pocket with a subperiosteal elevator and releasing the medial mandibular and mandibulocutaneous ligaments by detaching the periosteum from the mandible; FIG. 4E showing a photograph of an individual before a chin augmentation or enhancement disclosed herein; and FIG. 4F showing a photograph of the same individual after a chin augmentation or enhancement disclosed herein showing a superior clinical result whereby the implant lifts and improves the jowl;

FIG. 5B showing a top left perspective view; FIG. 5C showing a front plan view; and FIG. 5D showing a left plan view;

FIG. 6B showing a top left perspective view; FIG. 6C showing a front plan view; and FIG. 6D showing a left plan view;

FIG. 7B showing a top left perspective view; FIG. 7C showing a front plan view; and FIG. 7D showing a left plan view;

FIG. 8B showing a top left perspective view; FIG. 8C showing a front plan view; and FIG. 8D showing a left plan view;

FIGS. 9A-D is a single-piece mandibular implant disclosed herein comprising a mental arch and full left and right lateral arms with each arm comprising a ramus extension and being configured to extend along the jawline to its respective gonial angle with FIG. 9A showing a top plan view; FIG. 9B showing a top left perspective view; FIG. 9C showing a front plan view; and FIG. 9D showing a left plan view;

FIGS. 10A-D is a single-piece mandibular implant disclosed herein comprising a mental arch and full left and right lateral arms with each arm comprising a protrusion and ramus extension and being configured to extend along the jawline to its respective gonial angle with FIG. 10A showing a top plan view; FIG. 10B showing a top left perspective view; FIG. 10C showing a front plan view; and FIG. 10D showing a left plan view;

FIG. 11B showing a top left perspective view; FIG. 11C showing a front plan view; and FIG. 11D showing a left plan view;

FIG. 12B showing a top left perspective view;

FIG. 12C showing a front plan view; and FIG. 12D showing a left plan view;

FIG. 13B showing a top left perspective view; FIG. 13C showing a front plan view; and FIG. 13D showing a left plan view;

FIG. 14B showing a top left perspective view; FIG. 14C showing a front plan view; and FIG. 14D showing a left plan view.

DETAILED DESCRIPTION

Figure 1A:
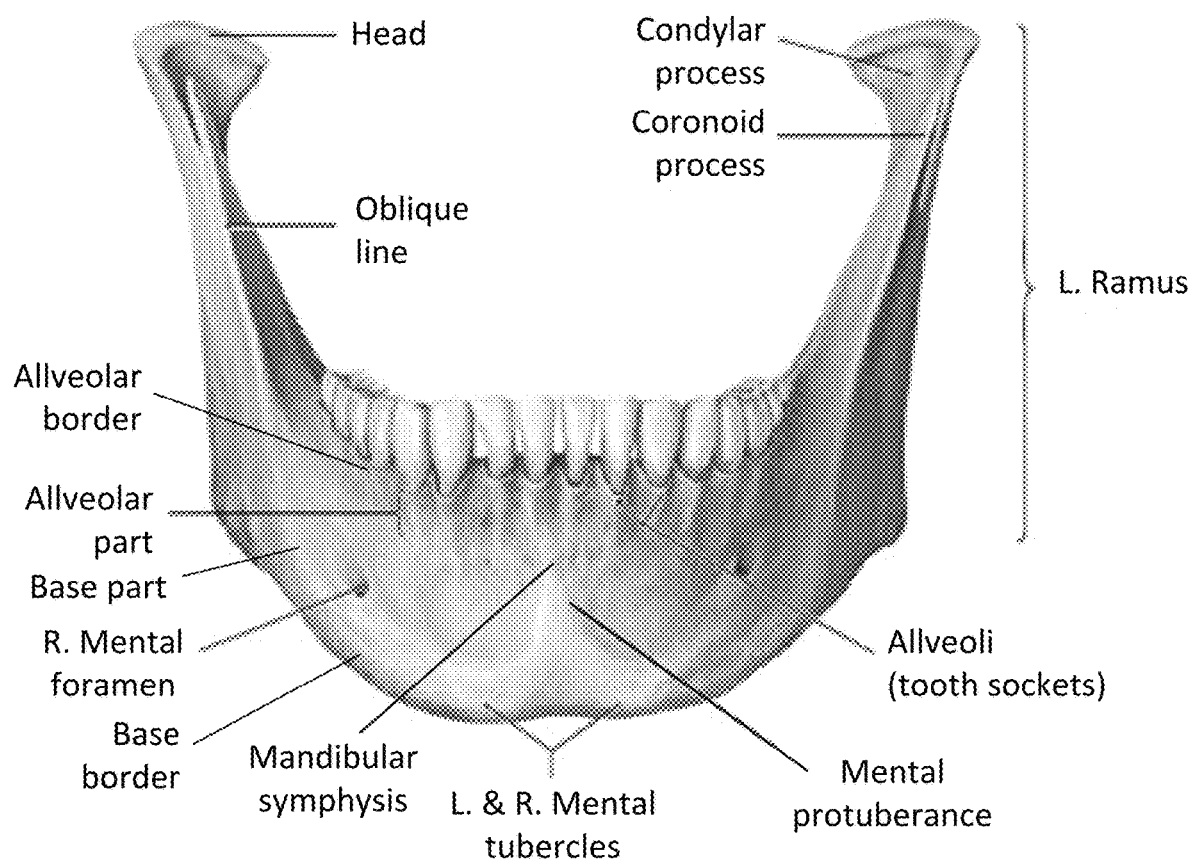
FIGS. 1A-C are illustrations of a human mandible with FIG. 1A showing an anterior view.
Figure 1B:
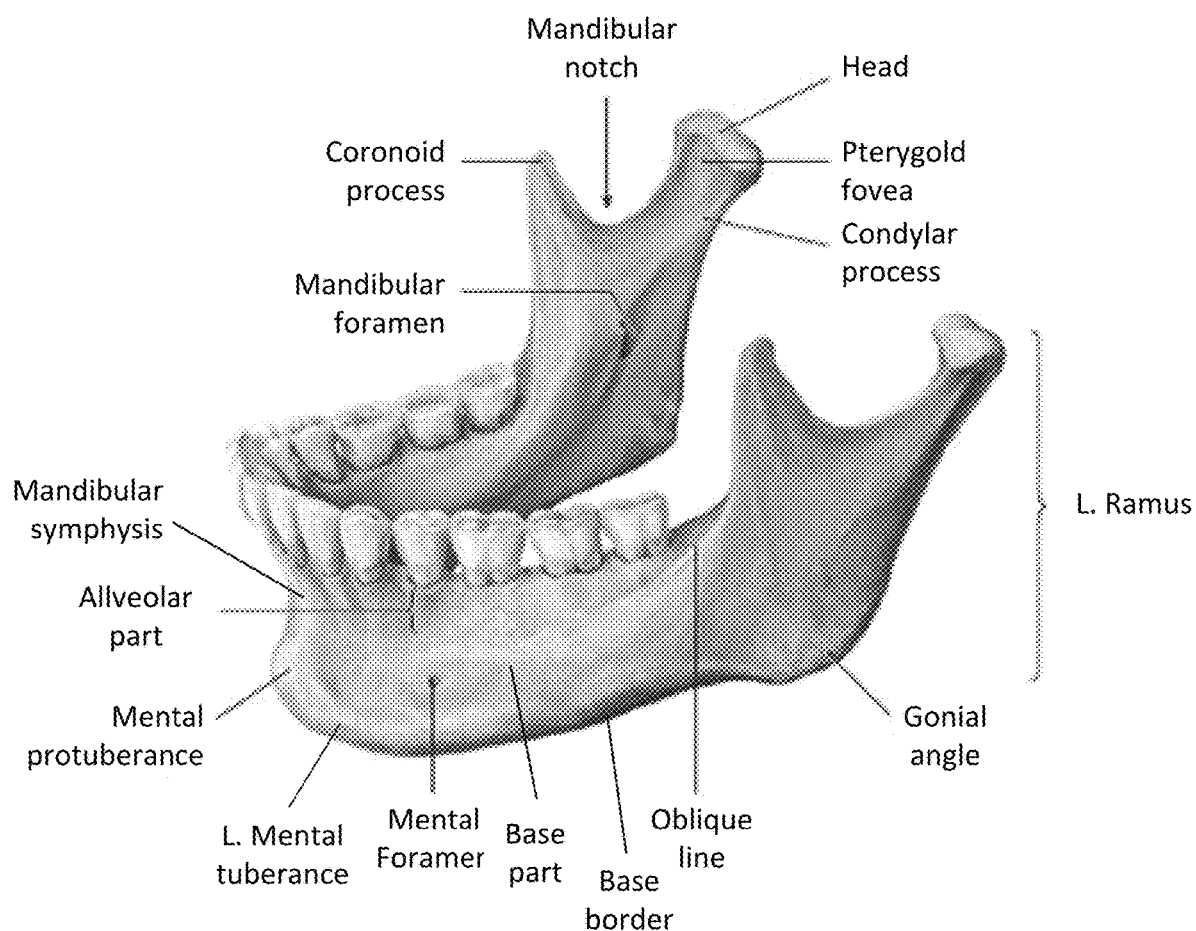
Figure 1C:
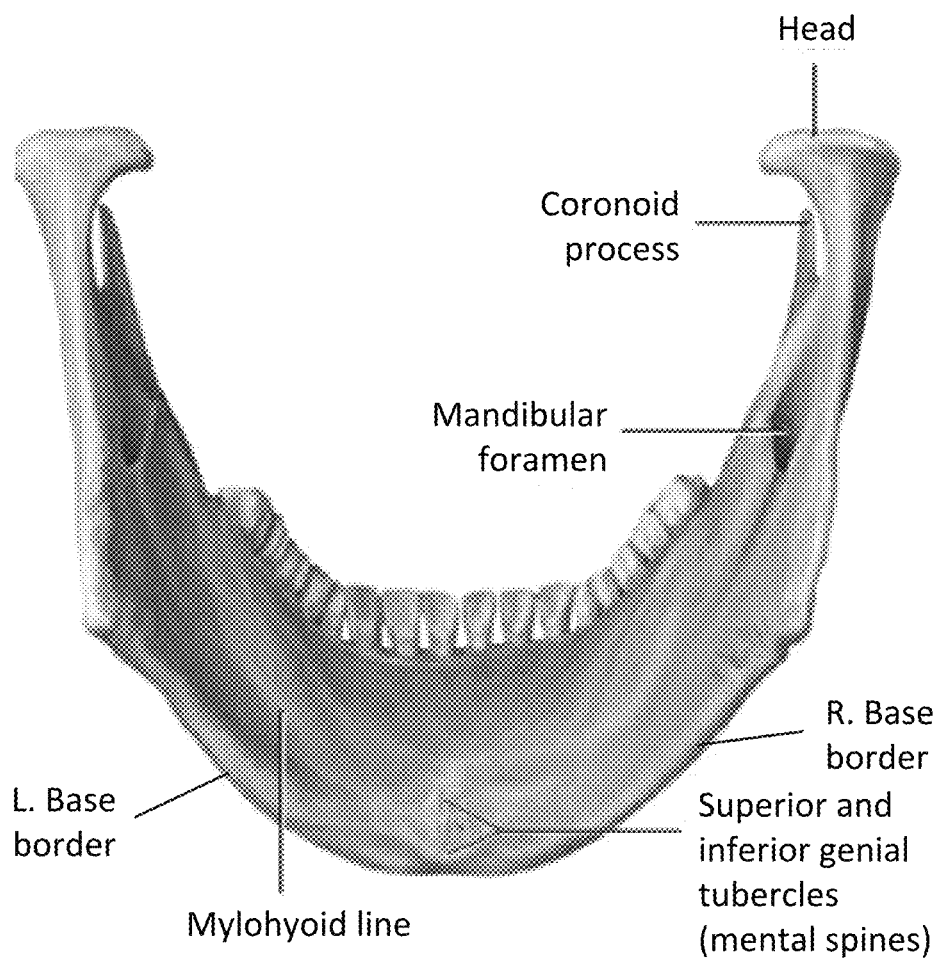

As illustrated in FIGS. 1A-C, the mandible is the largest bone in the human skull and comprises three parts, the central body, the left ramus and the right ramus. The body is the anterior portion of the mandible. The mandibular body is a substantially U-shaped structure, with a central front portion (or base of the U) and the two side portions (or stem of the U) and is bound by a superior alveolar border and inferior base border and external (or anterior) and internal (or posterior) surfaces. The alveolar border contains the hollow cavities in which the lower sixteen teeth reside while the base border forms the jawline.

Referring to FIGS. 1A & B, the central front portion of the mandibular body is generally rectangular in shape. Its external surface contains the mandibular symphysis, a midline ridge that divides this portion into two halves. The inferior end of the ridge expands laterally to give rise to the centrally located mental protuberance, a prominence that forms the chin. This prominence extends laterally from the left and right inferior portion of the mental protuberance to give rise to the left and right mental tubercles. The mandibular symphysis and superior edge of the mental protuberance and left and right mental tubercles create a left and right depression on either side of the midline. These two depressions each contain a mental foramen, an opening in which the mental nerve and vessels exit. The left- and right-side portions of the mandibular body are each curved rectangular in shape. The external surface of each can be divided into two portions, the superiorly located alveolar portion and the inferiorly located, horizontally curved base portion. The jawline is formed by the lower portions of the left and right mental tubercles and the lower portions of the base portion which together define the base border.

The left and right ramus are each a vertical process arising superiorly from each side portion of the mandibular body. The rami join the body at the angle of the mandible, also known as the gonial angle. At the superior aspect of each ramus, the coronoid and condylar processes articulate with the temporal bone to create the temporomandibular joint which permits mobility.

Covering the mandible is the periosteum. The periosteum is a dense irregular connective tissue divided into an outer "fibrous layer" and inner "cambium layer" (or "osteogenic layer"). The fibrous layer contains fibroblasts, while the cambium layer contains progenitor cells that develop into osteoblasts.

Figure 2A:
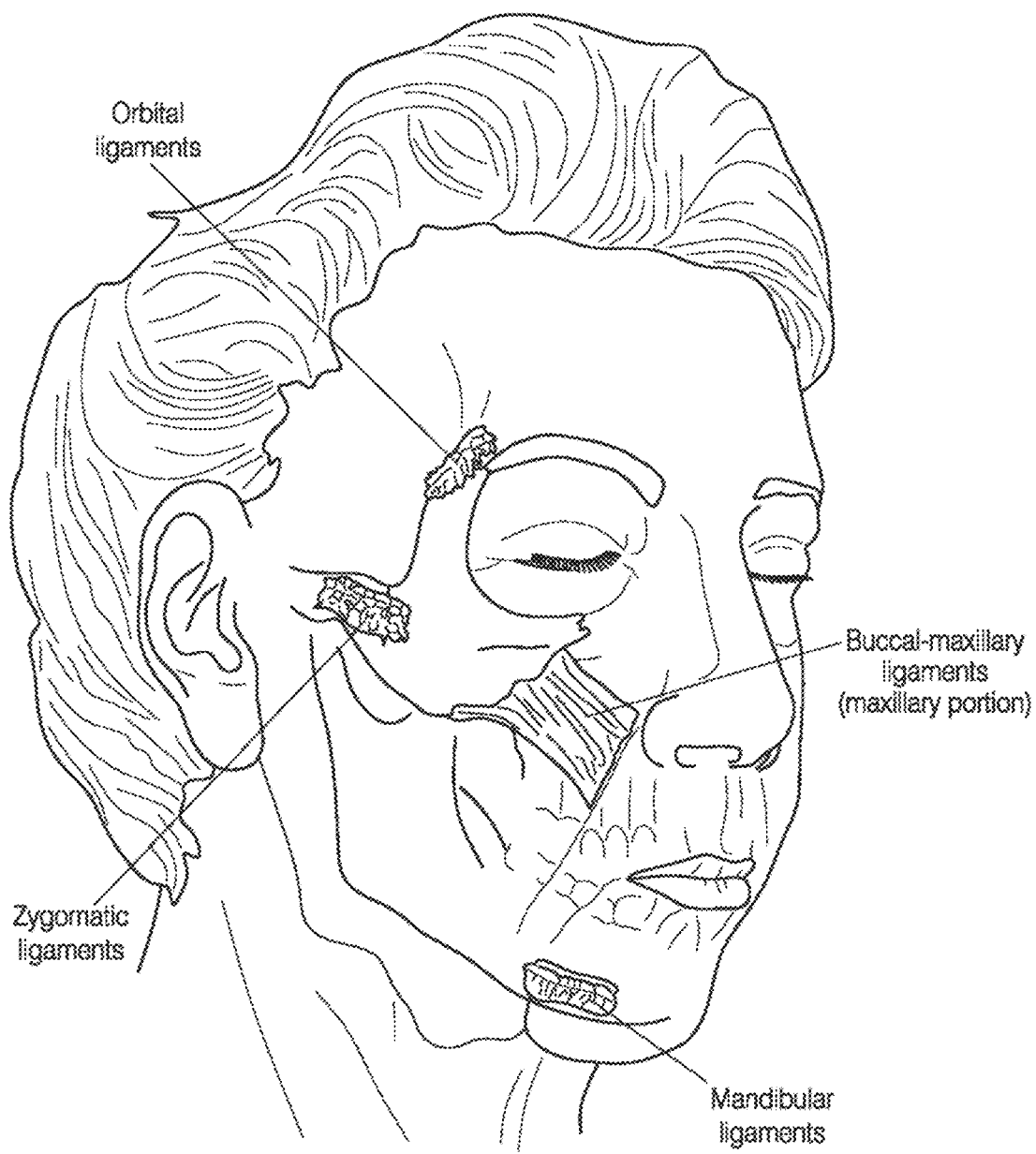
FIGS. 2A-B are illustrations of facial retaining ligaments with FIG. 2A showing true retaining ligaments supporting the subcutaneous tissues of the face.
Figure 2B:
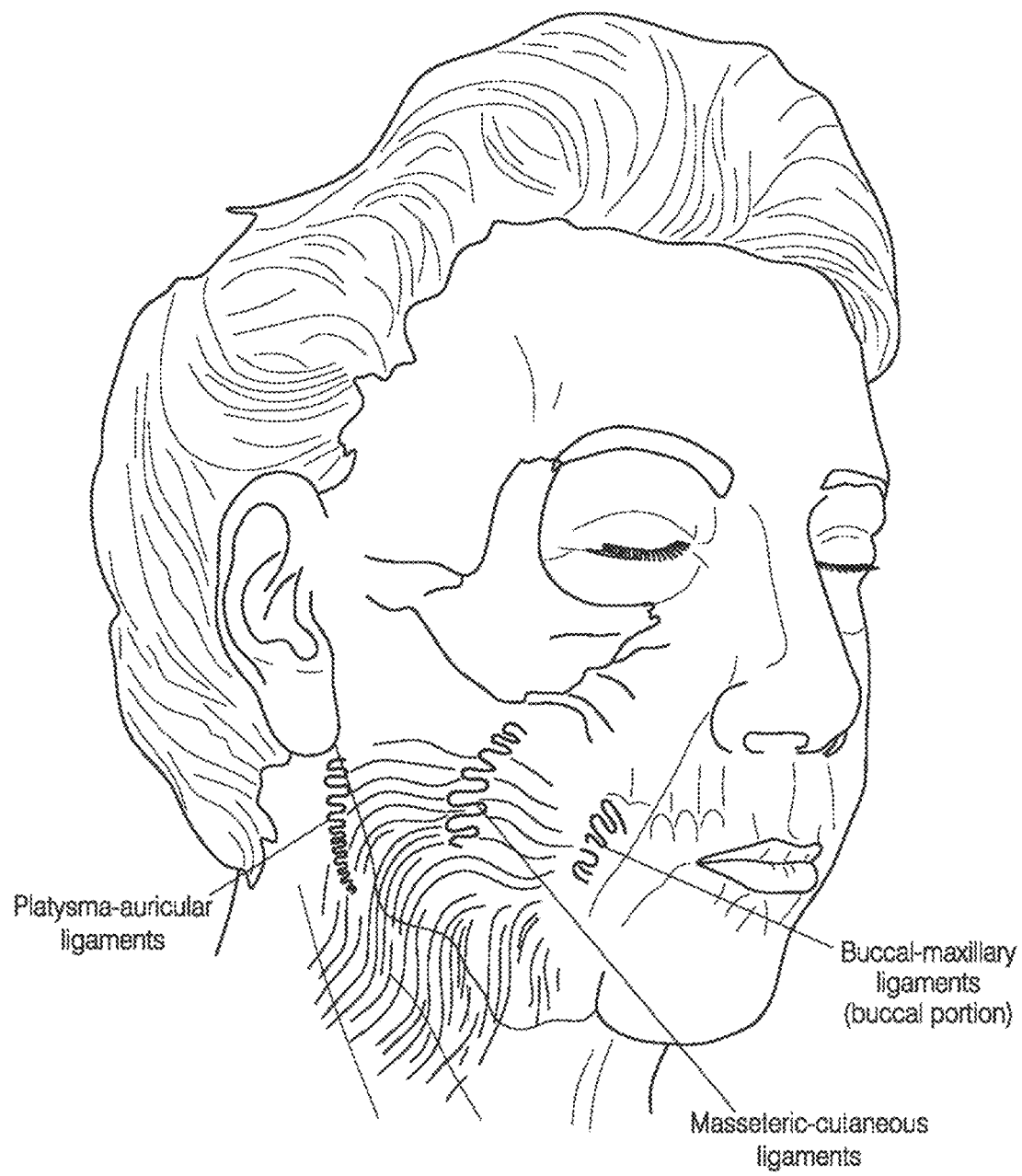

The retaining ligaments of the face are strong and deep fibrous attachments that originate from the periosteum or deep facial fascia and travel perpendicularly through facial layers to insert onto the dermis. These ligaments act as anchor points, retaining and stabilizing the skin and superficial fascia to the underlying deep fascia and facial skeleton in defined anatomic locations. Microscopically, each ligament is rooted in a tree-like distribution as a periosteal or deep fascial thickening that divides as it approaches the musculoaponeurotic system (SMAS) into numerous branches, which insert onto the dermis. This branching network of fibers is called the retinacular cutis, which is part of a larger complex system of fibrous septa in the subcutaneous layer. Retaining ligaments can be divided into "true retaining ligaments" and "false retaining ligament" (also referred to as septa or adhesions). True retaining ligaments are defined as ligaments that insert directly onto the dermis. As illustrated in FIG. 2A true retaining ligaments supporting the subcutaneous tissues of the face include the orbital ligaments, zygomatic ligaments, buccal-maxillary ligaments (maxillary portion), and the mandibular ligaments. True retaining ligaments are defined as ligaments that insert directly into the SMAS, and thus have an indirect effect on the dermis through the retinacular cutis. As illustrated in FIG. 2B false retaining ligaments of the face include the platysma-auricular ligaments, masseteric-cutaneous ligaments, and buccal-maxillary ligaments (buccal portion). The retaining ligaments of the face are important in understanding concepts of facial aging and rejuvenation. They are located in constant anatomic locations where they separate facial spaces and compartments. Their superficial extensions form subcutaneous septa that separate facial fat compartments.

During the past 30 years there have been several concepts of face lift surgery advanced. Starting with a "skin lift", then advancing to a superficial musculoaponeurotic system (SMAS) and extended SMAS dissection, the "deep plane facelift" and then by popularizing the "endoscopic forehead lift" which then extended inferiorly into the "subperiosteal" face lift. However, common problems with a subperiosteal face lift include the fact that the retaining ligaments of the face and the periosteum do not stretch and the periosteum, once elevated, adheres quickly back to the bone. As such, most of the benefit of the periosteal face lift is diminished and many patients with conventional face lifts have questioned the reduced longevity of their face lifts.

Without wishing to be limited to any particular theory, one inventive aspect of the present specification relies on the discover of an aponeurotic condensation of fibrous tissue, referred to herein as the anterior mental fibrous condensation. The present specification is based on the finding that severing of the left and right anterior mental fibrous condensations at its periosteal insertion site(s) in conjunction with surgical manipulation of the left and right mandibular ligaments can unexpectedly and surprisingly provide synergistic benefits to a mandibular augmentation or enhancement procedure as well as to a face lift procedure. For example, a method disclosed herein synergistically mobilizes the mental soft tissue and volumetrically augments the chin above and beyond what would be expected of implanting a chin implant alone. In addition, the surgical manipulation disclosed herein provides an improved surgical procedure for mandibular augmentation or enhancement by greatly expanding the location a mandibular implant can be positioned. Furthermore, since the disclosed surgical procedure increases the location where a mandibular implant can be implanted, novel chin implants of new sizes and shapes can now be created and advantageously used. Lastly, the disclosed method enables a mandibular implant to also be advantageously used as a spacer to prevent or reduce re-adherence of the periosteum with its overlying soft tissue back to the bone. The inhibition or reduction of periosteum re-attachment to the mandible, ensure that the soft tissue of the face remains elevated. As such, the disclosed method enhance conventional face lift procedures by preventing or reducing the expected postoperative recurrence of soft tissue retraction back to its preoperative position.

Figure 3A:
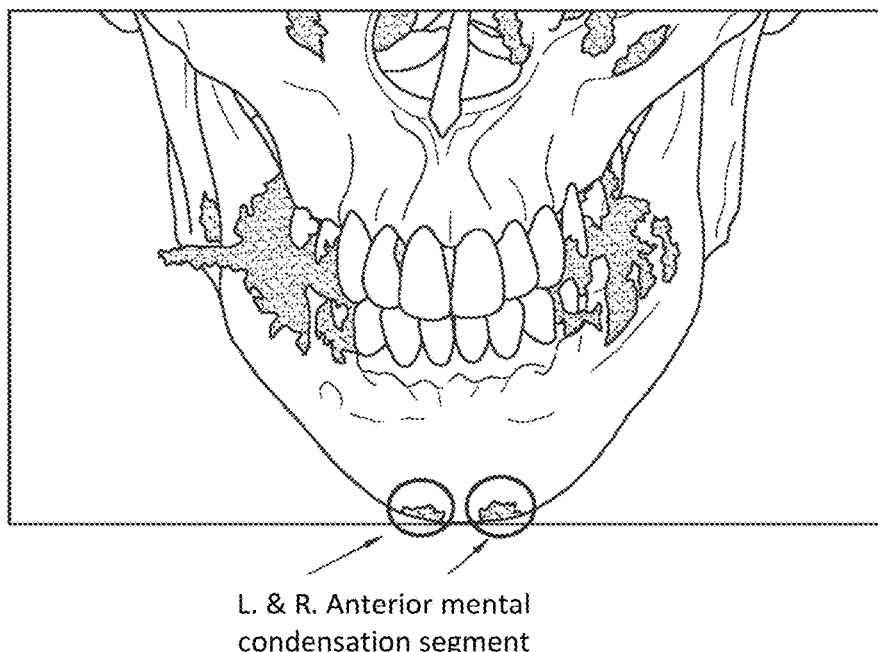
FIGS. 3A-B are illustrations of facial condensation segments and retaining ligaments of the mandible with FIG. 3A showing the position of the left and right anterior mental fibrous condensation segments.

The disclosed method of mandibular augmentation or enhancement comprises the surgical manipulation of the left and right anterior mental fibrous condensations in conjunction with the anatomy of the left and right mandibular ligaments. As illustrated in FIGS. 3A & B, the left and right anterior mental fibrous condensations are located on the mental tubercles of the mandible. An aponeurotic condensation of fibrous tissue, each anterior mental fibrous condensation has been found to typically include a plurality of anterior mental fibrous condensation segments spaced apart as illustrated in FIG. 3A, although they may not be segmented or spaced apart depending on an individual patient's anatomy. Each anterior mental fibrous condensation is woven into the periosteum at a deep origination site at the left and right mental tubercles and extends and inserts through the soft tissue layers.

Figure 3B:
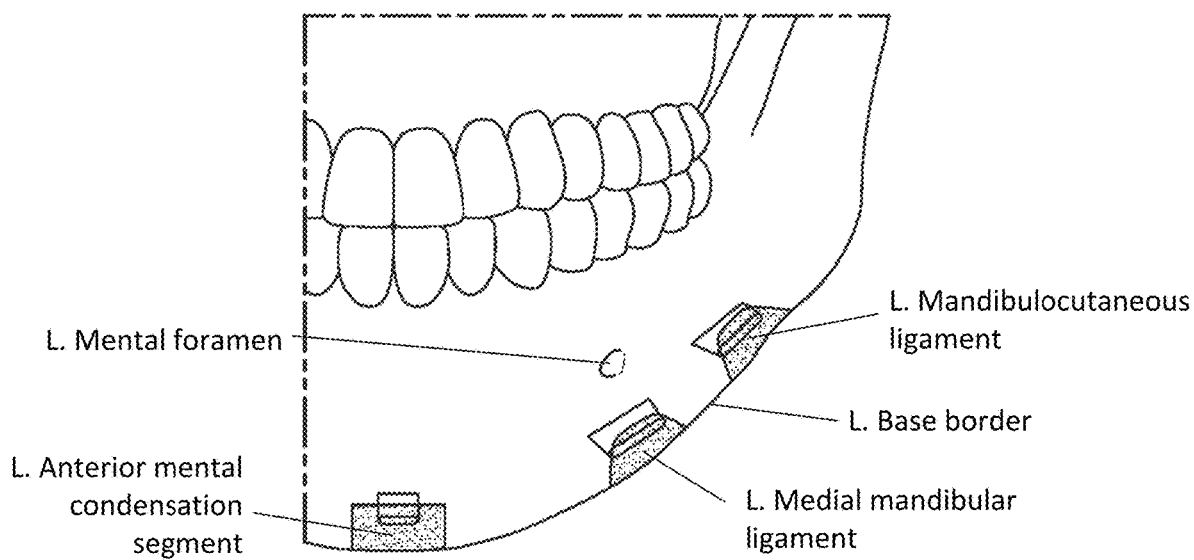

As illustrated in FIGS. 2A & 3B, the left and right mandibular ligaments are retaining ligaments that originate from the periosteum and inserts directly into the dermis to create strong and deep fibrous attachments. The left and right mandibular ligaments are lateral to the left and right anterior mental fibrous condensations, respectively. Measuring about 2 cm horizontally and about 1.2 cm vertically, these ligaments are located about 4.5 cm anterior to the gonial angle of the mandible, inferior to the left and right mental foramen, and about 1 cm superior the base border of the mandible. The left and right mandibular ligaments are each composed of two distinct fibrous attachments located about 2 mm to about 3 mm from each other called the medial mandibular ligament and the mandibulocutaneous ligaments.

In some embodiments, and as shown in FIGS. 4A-D, a disclosed method of mandibular augmentation or enhancement comprises 1) accessing one or more segments of the left and/or right anterior mental fibrous condensation; 2) releasing the one or more segments of the left and/or right anterior mental fibrous condensation; 3) subperiosteally releasing one or more mandibular ligaments to form an implantation cavity; and 4) inserting a mandibular implant into the implantation cavity.

Figure 4A:
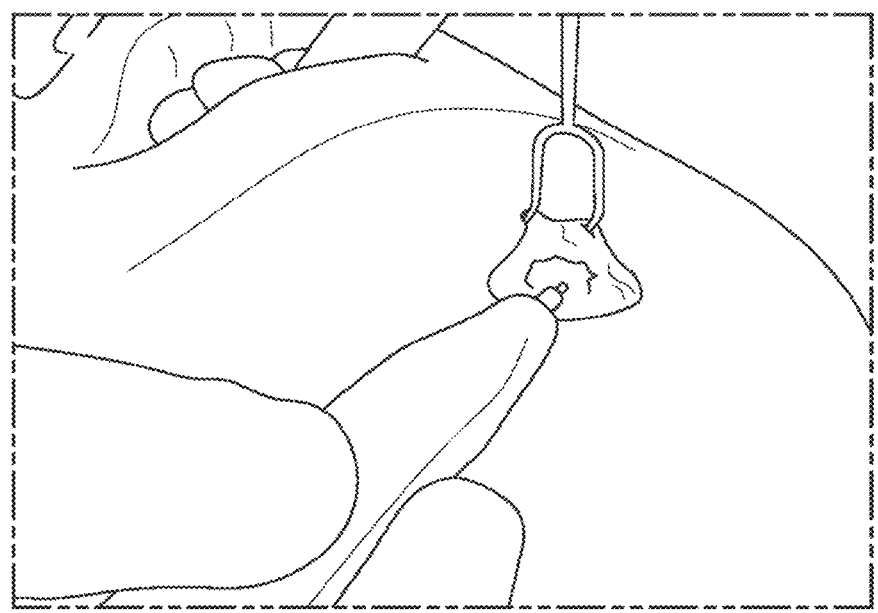
FIGS. 4A-4F show steps of a method of performing a chin augmentation or enhancement disclosed herein inserting of a mandibular implant disclosed herein from mentum to gonial angle with FIG. 4A illustrating the incision of the skin, fascia, and periosteum down to the bone.

In some embodiments, a method disclosed herein comprises accessing one or more segments of a left and/or right anterior mental fibrous condensation can be accomplished by creating an incision in the skin, as illustrated in FIG. 4A. In some embodiments, accessing one or more segments of a left and/or right anterior mental fibrous condensation can be accomplished by creating an incision in the skin within the submental space. For example, an inverted V-shaped incision which approximately follows the jawline can be made posteriorly to the base border and then dissecting through the soft tissue underlying the incision site until the one or more attachment points of the one or more segments of the left and/or right anterior mental fibrous condensations on exterior surface of the mandible are identified. In some embodiments, accessing the segments of the anterior mental fibrous condensation can be accomplished by creating an intraoral incision through the vestibule of the mouth. For example, an incision can be made proximate to the mental protuberance, and then dissecting deep through the soft tissue underlying the incision site. Once the sub-periosteal level is reached by deepening and extending the dissection, the one or more attachment points of the one or more segments of the left and/or right anterior mental fibrous condensations on exterior surface of the mandible can then be identified.

Figure 4B:
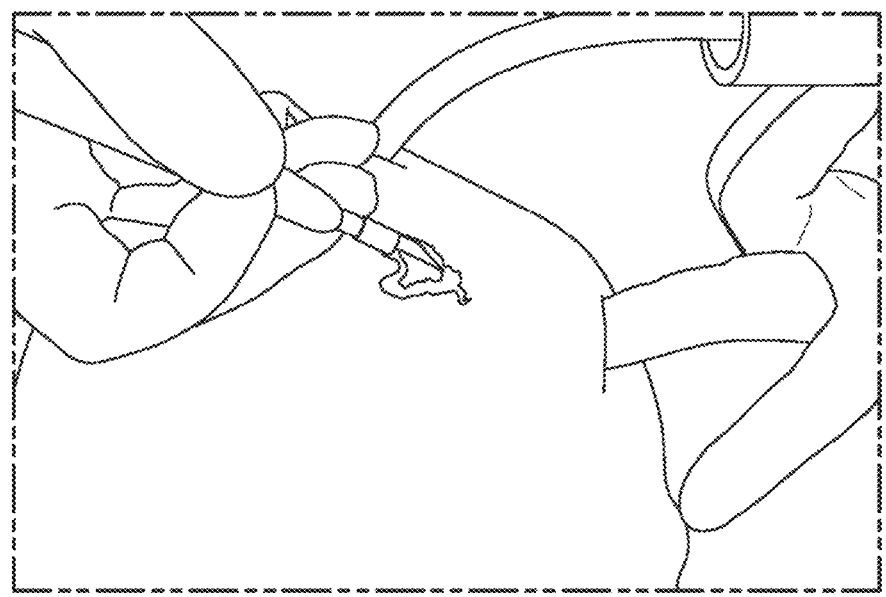

In some embodiments, a method disclosed herein comprises releasing one or more segments of the left and/or the right anterior mental fibrous condensation from it mandibular attachment point. Once identified, the one or more segments of the left and/or right anterior mental fibrous condensations are incised and released at the subperiosteal and periosteal level at their attachment sites located on the mental tubercles of the mandible, as illustrated in FIG. 4B. In some embodiments, the one or more segments of the left and right anterior mental fibrous condensations can be release by excising and severing their respective attachment sites located on the mental tubercles of the mandible using a cutting device, such as, e.g., a scalpel, a scissors, an electromagnetic energy device (e.g., electrocautery) and the like.

Figure 4C:
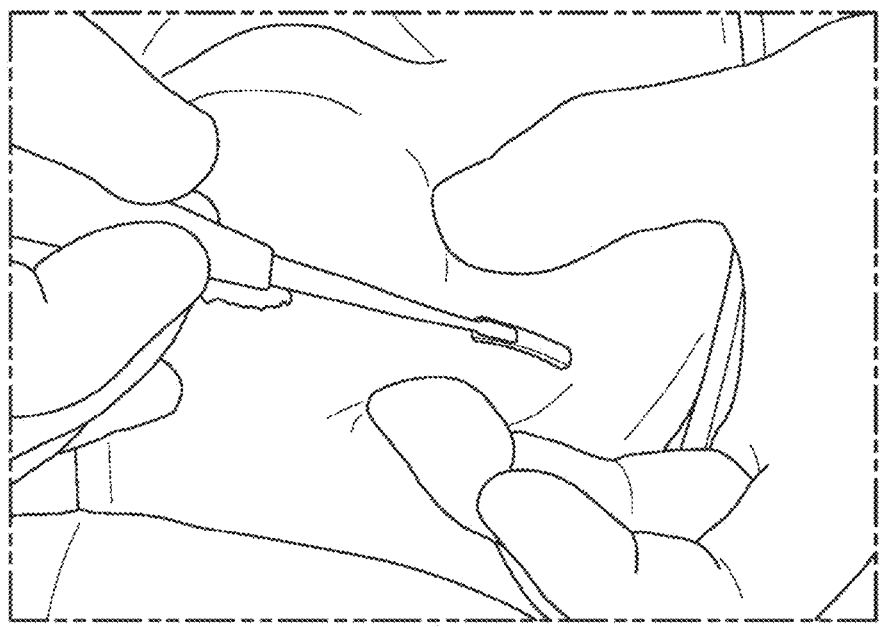

In some embodiments, a method disclosed herein comprises subperiosteally releasing one or more mandibular ligaments from their one or more mandibular attachment points to form a subperiosteal implantation cavity. After the one or more segments of the left and/or right anterior mental fibrous condensations are released, the left and right mandibular ligaments and overlying soft tissue can then be released from the body of the mandible to form a subperiosteal implantation cavity or pocket. In some embodiments, the left and/or right mandibular ligaments and overlying soft tissue are released from the body of the mandible by blunt dissection of the medial mandibular and mandibulocutaneous ligaments at the subperiosteal level using a periosteal elevator. As shown in FIGS. 4B & C, finger placement locates the position of the mental foramen and jawline and this technique safely keeps the subperiosteal dissection within the area of the lower border of the body of the mandible and well below the mental foramen and exiting mental nerve which allows for simple and safe access to the parasymphyseal areas. Once the one or more mandibular ligaments are elevated from the bony surface at the subperiosteal level, continued blunt dissection can be easily extend the subperiosteal implantation cavity or pocket laterally without resistance. A subperiosteal implantation cavity or pocket can be extended laterally any distance past an attachment site of a mandibulocutaneous ligament. In some embodiments, a subperiosteal implantation cavity or pocket can be extended laterally any distance past an attachment site of a mandibulocutaneous ligament and up to a gonial angle of the mandible. In some embodiments, a subperiosteal implantation cavity or pocket can be extended laterally midway between an attachment site of a mandibulocutaneous ligament and a gonial angle of the mandible. In some embodiments, a subperiosteal implantation cavity or pocket can be extended laterally all the way to the gonial angle of the mandible. As shown in FIG. 4C, the placement of a periosteal elevator over the jawline illustrates the direction and location that a subperiosteal pocket can be formed using the disclosed method.

Figure 4D:
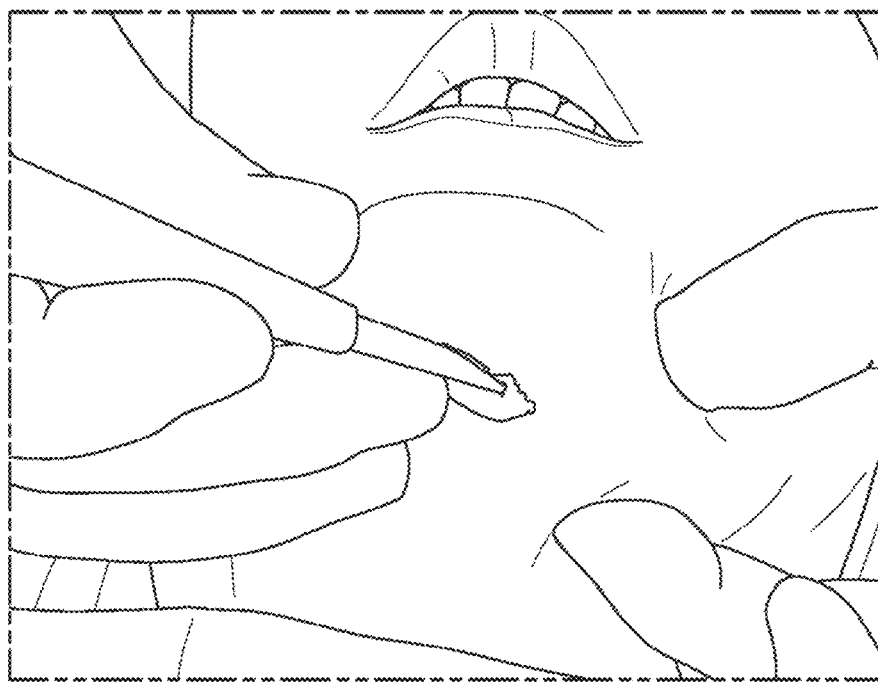

In some embodiments, a method disclosed herein comprises inserting of a mandibular implant into the implantation cavity. As depicted in FIG. 4D, a larger pocket is able to be created once the medial mandibular and mandibulocutaneous ligaments are elevated and the subperiosteal implantation cavity is extended to the desired length, so that a larger and variable shaped mandibular implant can then be inserted into the cavity. Correct implant placement can be highly advantageous in creating an improved aesthetic result. Implant placement can be at the lower border of the mandible, and not at a higher location, as release of the left and right anterior mental fibrous condensations in conjunction with the left and right mandibular ligaments allows for this proper positioning of a mandibular implant. In some embodiments, a mandibular implant can be placed such that the inferior border of the implant at the midline of the mandible is at, or within about 2 cm, about 1.5 cm, about 1 cm, about 0.5 cm, or less from the midline of the chin, (with attachment to the mental tubercle) and the base border of the mandible. Once placement of the mandibular implant is finalized, the skin incision is closed to complete a method of mandibular augmentation or enhancement disclosed herein.

The method disclosed herein releases the surrounding soft tissue to enable this tissue to rotate and advance without restriction. This not only advantageously increases anterior projection, but upon rotation of the soft tissue (from the submental area) increases the appearance of vertical dimension to the entire anterior mandibular area as well. Also by elevating and allowing the soft tissue at the medial mandibular and mandibulocutaneous ligaments to be repositioned upward and outward, it has the ability to overall exponentially add volume to the entire area; thus providing an unexpected, synergistic benefit in all dimensions in the appearance to the entire lower ⅓ of the face. Such results would not otherwise be achievable with just the placement of an ordinary mandibular implant without addressing the anterior mental fibrous condensation and/or the mandibular ligaments.

In some embodiments, mandibular implants can include inferior and/or anterior extensions to the implant inserted below the incised body structures and laterally to ensure that the area of bone at the attachment of the medial mandibular and mandibulocutaneous ligaments is completely covered to ensure the periosteum remains elevated and does not re-attach to the underlying bone. In some embodiments, a mandibular implant incorporates a section to ensure that the implant is inserted beneath the structures which are released and/or surgically elevated along with the periosteum, or other structures and/or geometries as further described herein.

In some embodiments, the synergistic augmentation volume provided by a method disclosed herein above and beyond the volume of the implant. The volume could project, for example, evenly or unevenly in one or more of the anterior-posterior and/or vertical dimension with different percentage values or ranges as disclosed above. In some embodiments, the synergistic augmentation volume provided by a method disclosed herein above and beyond the volume of the implant can be, e.g., about 10%, about 20%, about 30%, about 40%, about 50%, about 60%, about 70%, about 80%, about 90%, about 100%, or more. In some embodiments, the synergistic augmentation volume provided by a method disclosed herein above and beyond the volume of the implant can be, e.g., at least 10%, at least 20%, at least 30%, at least 40%, at least 50%, at least 60%, at least 70%, at least 80%, at least 90%, at least 100%, or more. In some embodiments, the synergistic augmentation volume provided by a method disclosed herein above and beyond the volume of the implant can be, e.g., at most 10%, at most 20%, at most 30%, at most 40%, at most 50%, at most 60%, at most 70%, at most 80%, at most 90%, at most 100%. In some embodiments, the synergistic augmentation volume provided by a method disclosed herein above and beyond the volume of the implant can be, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%.

Figure 4E:
Figure 4F:
Figure 5A:
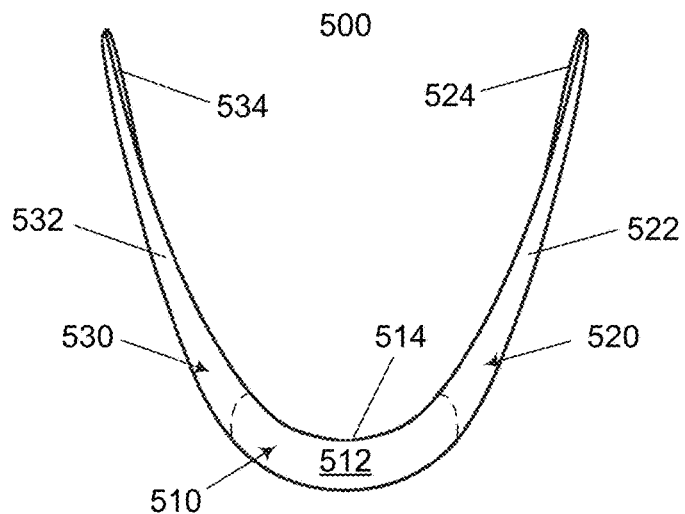
FIGS. 5A-D is a single-piece mandibular implant disclosed herein comprising a mental arch and thin left and right lateral arms with each arm being configured to extend along the jawline to its respective gonial angle with FIG. 5A showing a top plan view.
Figure 5B:
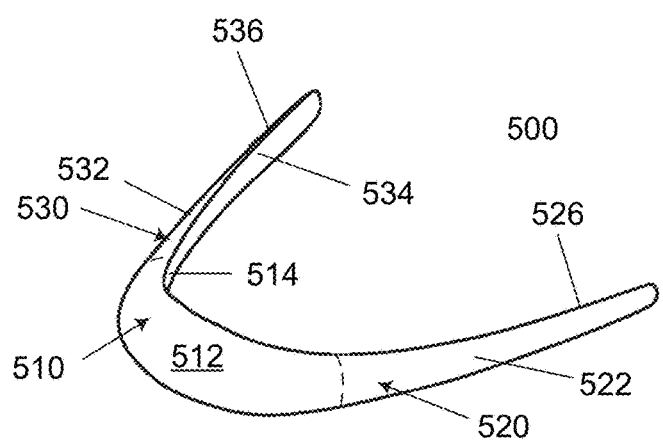
Figure 5C:
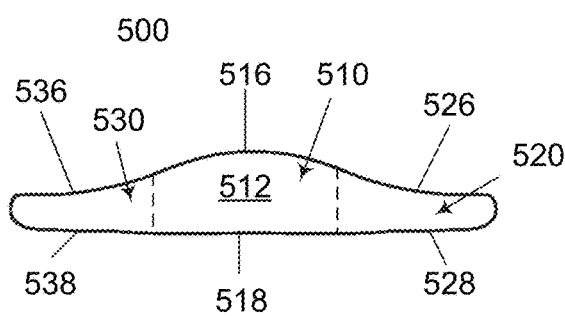
Figure 5D:
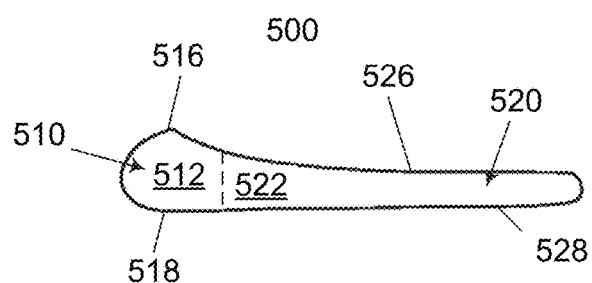
Figure 6A:
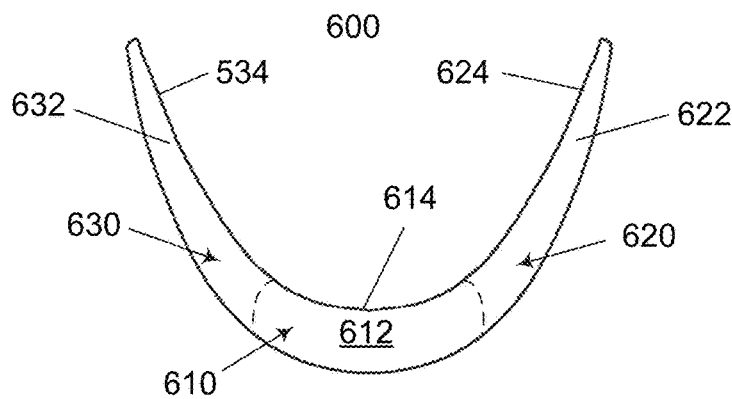
FIGS. 6A-D is a single-piece mandibular implant disclosed herein comprising a mental arch and full left and right lateral arms with each arm being configured to extend along the jawline to midway between its respective mental foramen and gonial angle with FIG. 6A showing a top plan view.
Figure 6B:
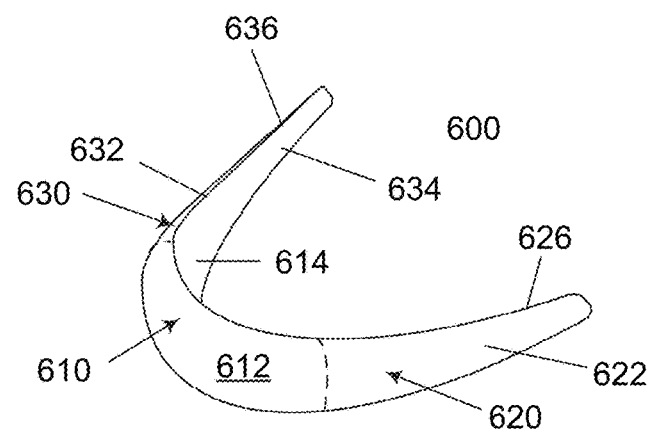
Figure 6C:
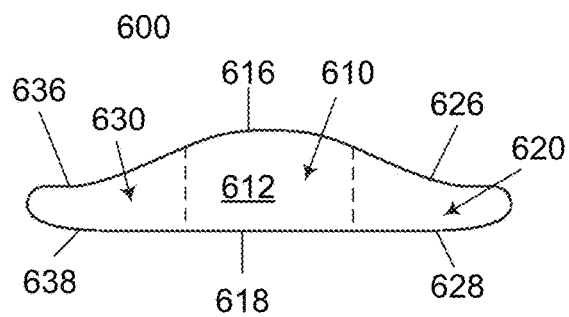
Figure 6D:
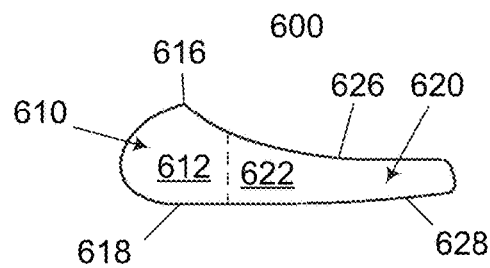
Figure 7A:
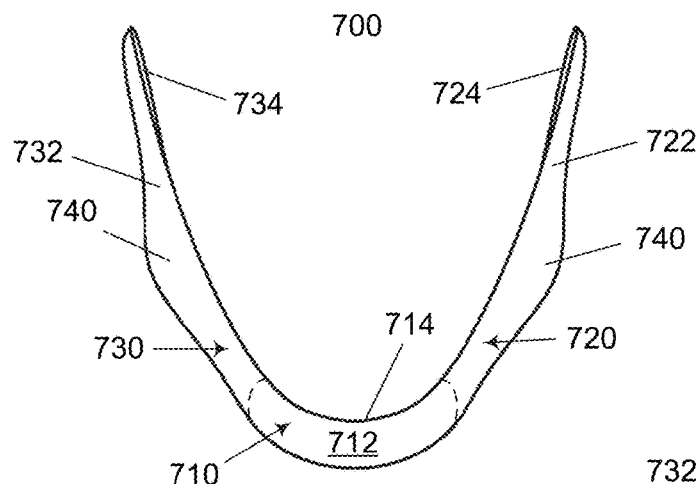
FIGS. 7A-D is a single-piece mandibular implant disclosed herein comprising a mental arch and full left and right lateral arms with each arm comprising a protrusion and being configured to extend along the jawline to its respective gonial angle with FIG. 7A showing a top plan view.
Figure 7B:
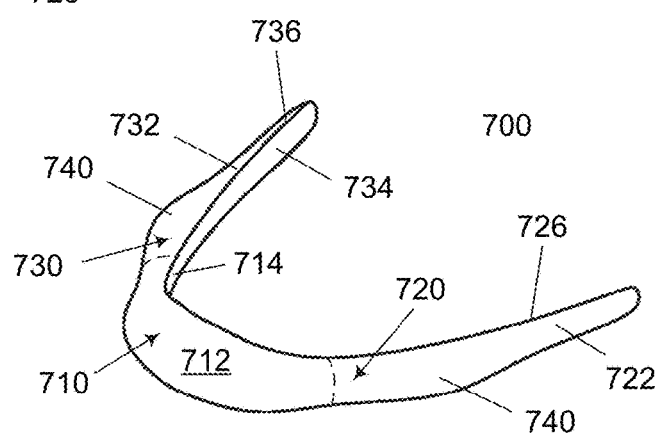
Figure 7C:
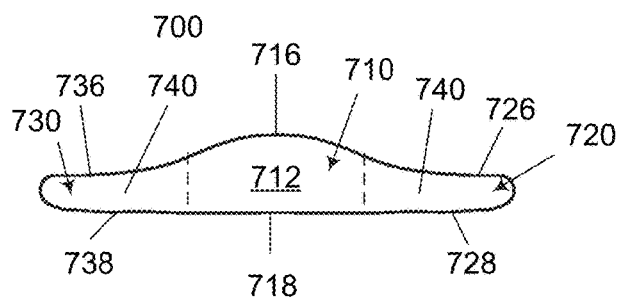
Figure 7D:
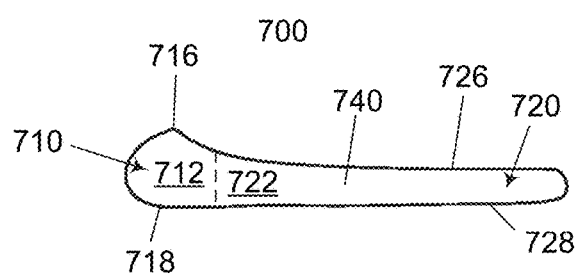
Figure 8A:
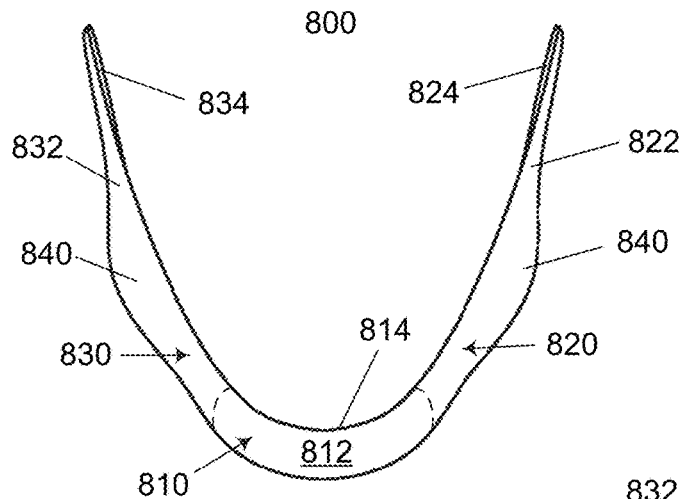
FIGS. 8A-D is a single-piece mandibular implant disclosed herein comprising a mental arch and full left and right lateral arms with each arm comprising a protrusion and being configured to extend along the jawline to its respective gonial angle with FIG. 8A showing a top plan view.
Figure 8B:
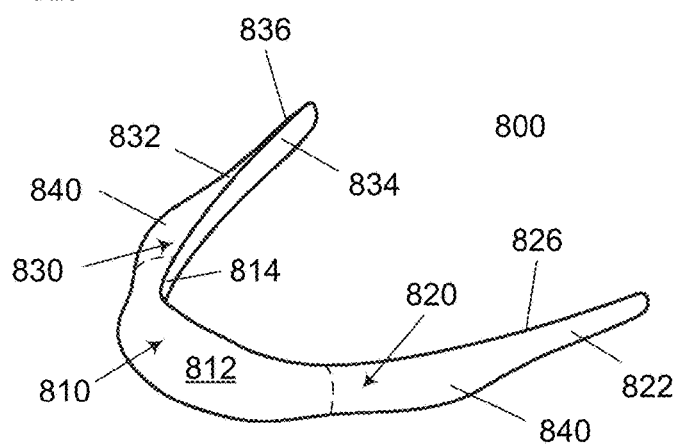
Figure 8C:
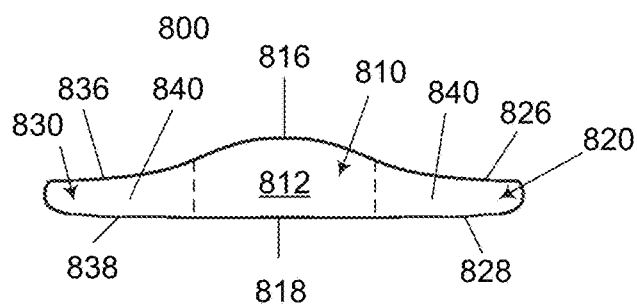
Figure 8D:
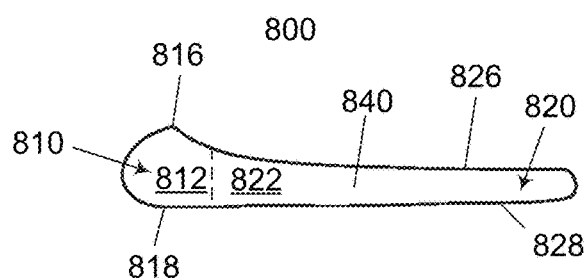
Figure 11A:
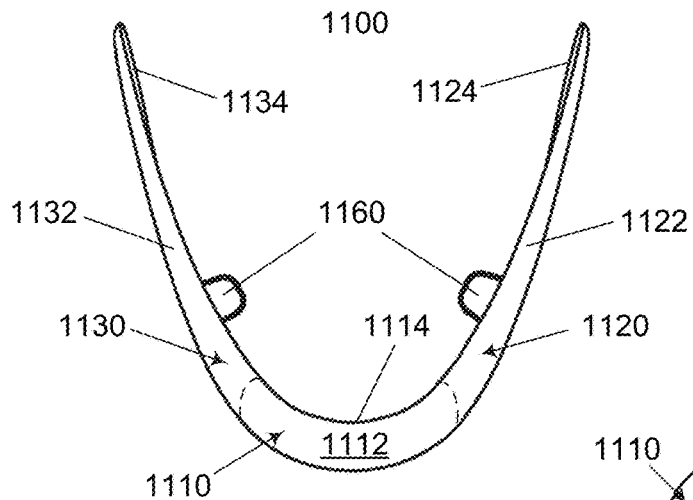
FIGS. 11A-D is a single-piece mandibular implant disclosed herein comprising a mental arch and full left and right lateral arms with each arm comprising a base tab on its inner surface and being configured to extend along the jawline to its respective gonial angle with FIG. 11A showing a top plan view.
Figure 11B:
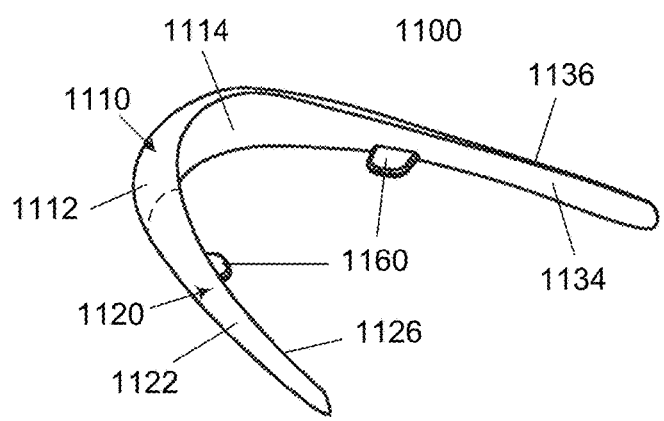
Figure 11C:
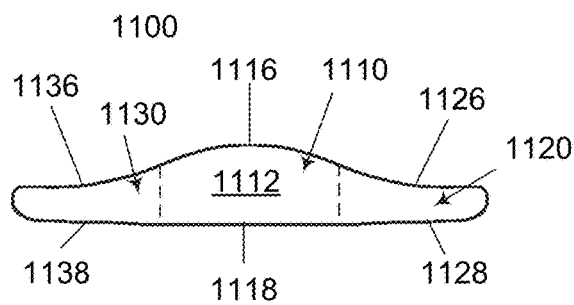
Figure 11D:
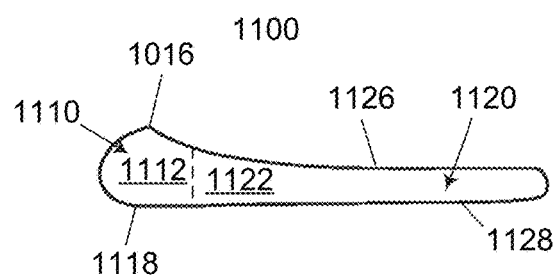
Figure 12A:
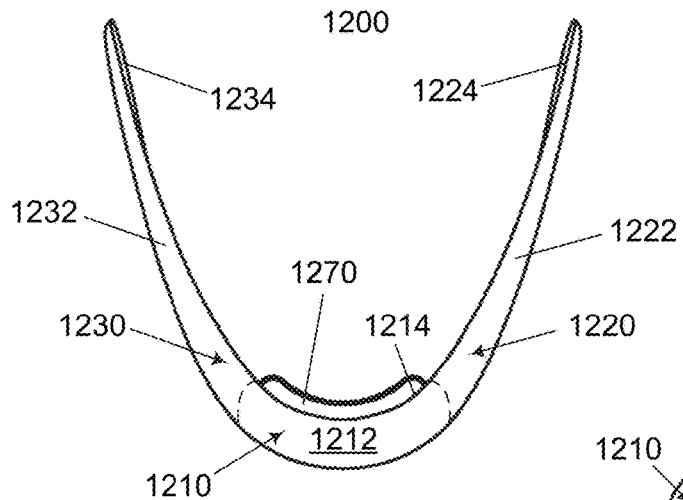
FIGS. 12A-D is a single-piece mandibular implant disclosed herein comprising a mental arch and full left and right lateral arms with the mental arch comprising a submental tab located on its inner surface and each arm being configured to extend along the jawline to its respective gonial angle with FIG. 12A showing a top plan view.
Figure 12B:
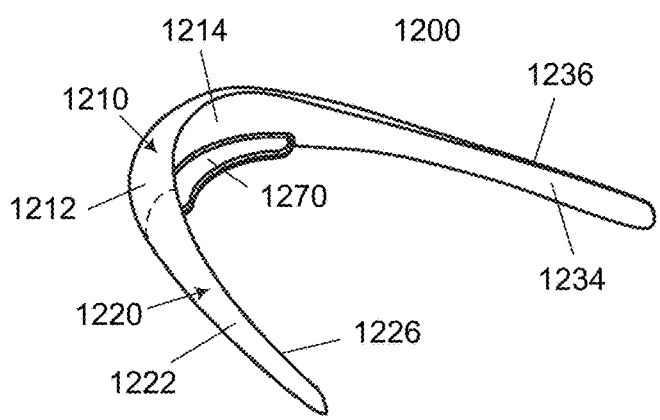
Figure 12C:
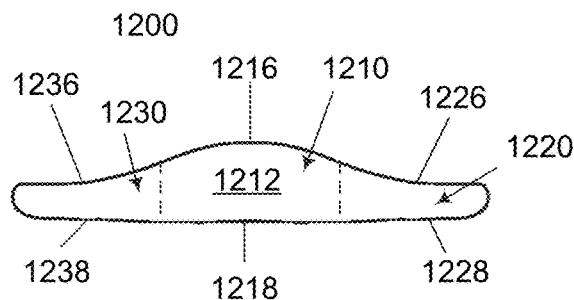
Figure 12D:
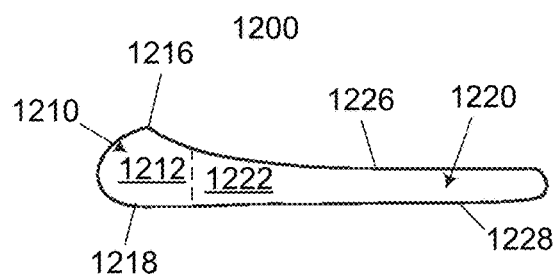
Figure 13A:
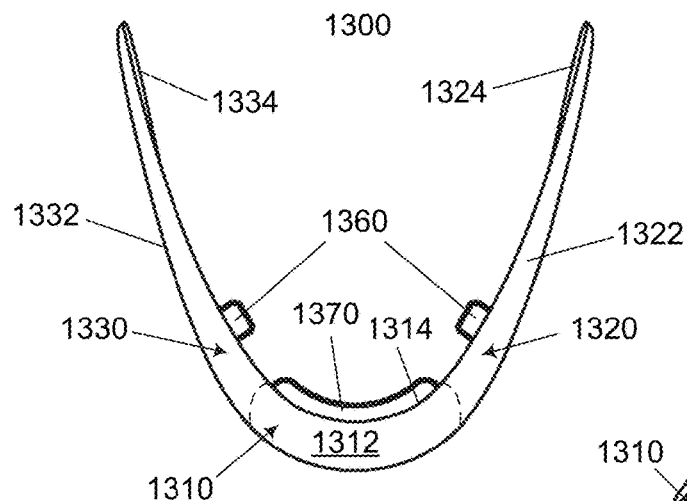
FIGS. 13A-D is a single-piece mandibular implant disclosed herein comprising a mental arch and full left and right lateral arms with the mental arch comprising a submental tab located on its inner surface and each arm comprising a base tab on its inner surface and being configured to extend along the jawline to its respective gonial angle with FIG. 13A showing a top plan view.
Figure 13B:
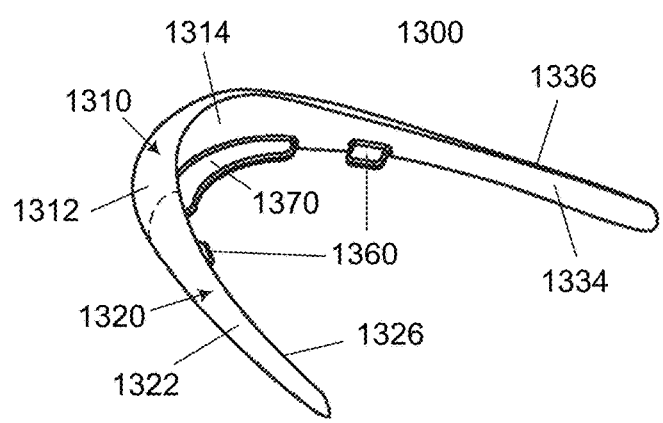
Figure 13C:
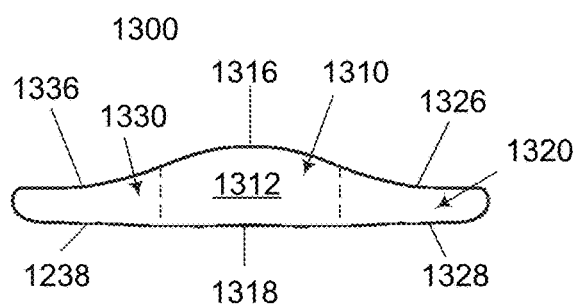
Figure 13D:
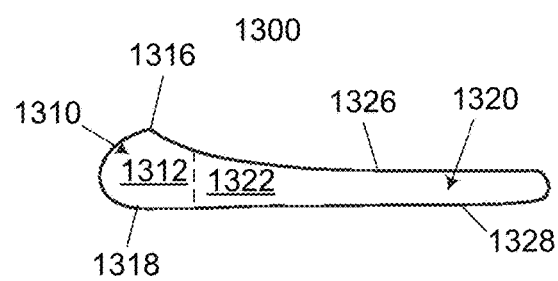
Figure 14A:
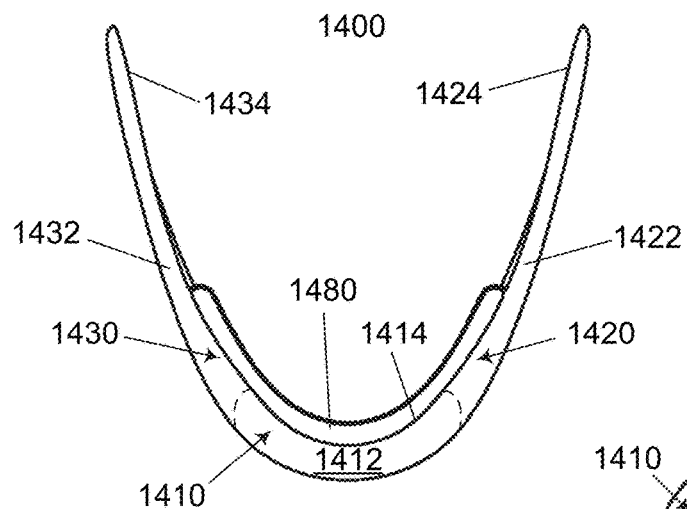
FIGS. 14A-D is a single-piece mandibular implant disclosed herein comprising a mental arch and full left and right lateral arms with each arm being configured to extend along the jawline to its respective gonial angle and the implant comprising an extended tab on the inner surface of the mental arch which extends into a portion of each arm with FIG. 14A showing a top plan view.
Figure 14B:
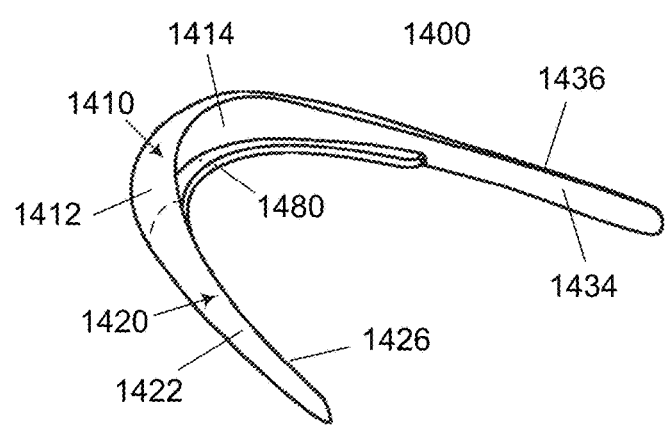
Figure 14C:
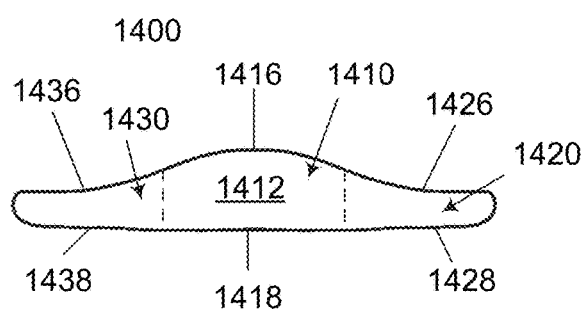
Figure 14D:
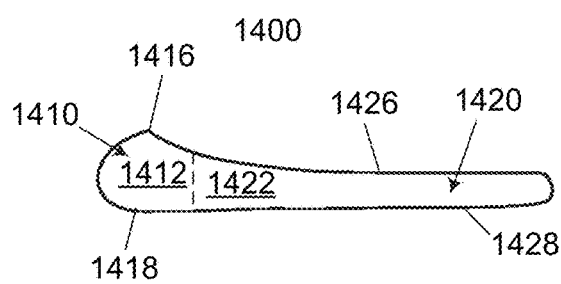

In some embodiments, a method disclosed herein can substantially improve the jowls. For example, FIG. 4E shows a photograph of an individual before a mandibular augmentation or enhancement using a method disclosed herein while FIG. 4F show a photograph of the same individual after insertion of a mandibular implant (from mentum to gonial angle) that displaces the soft tissue, and smooths out the adjacent soft tissue depressions or deficiencies using a method disclosed. FIG. 4F clearly shows a superior clinical result of a mandibular augmentation or enhancement using a method disclosed herein whereby the implant lifts and improves the jowl.

It is known that facial implants are used to augment or project out over a designated area of the facial skeleton by virtue of their volume and particular geometry. In some embodiments, a face lift (e.g. rhytidectomy) procedure is performed concurrently with a method of mandibular augmentation or enhancement disclosed herein. In some embodiments, any number of the true ligaments of the cheek or forehead, such as, e.g., the orbital ligaments, zygomatic ligaments, buccal-maxillary ligaments (maxillary portion) can be incised, excised, or released (and/or left alone and untouched). In some embodiments a method disclosed herein does disturb or excise true ligaments of the cheek or forehead. In some embodiments, any number of the false ligaments of the cheek or forehead, such as, e.g., the platysma-auricular ligaments, masseteric-cutaneous ligaments, and buccal-maxillary ligaments (buccal portion) can be incised, excised, or released (and/or left alone and untouched). In some embodiments a method disclosed herein does disturb or excise false ligaments of the cheek or forehead. In some embodiments, no face lift procedure is required or performed in conjunction with a method of mandibular augmentation or enhancement disclosed herein.

In some embodiments, a method disclosed can include augmenting a facial feature with one or more dermal filler materials, e.g., injected into a region of the face such as the chin, in addition to, or instead of implanting a long-term implant.

While described primarily with respect to treating the chin, some embodiments of the invention can also be used or modified for use with other anatomical regions, including the mid-face, other areas of the face, or other parts of the body, for example.

Given the distinct implant pockets that can be created, a variety of chin implants can be utilized with methods and uses as disclosed herein. The chin implants could be conventional, or also include improved mandibular implants as disclosed herein. For example is some embodiments, a mandibular implant disclosed herein is configured to augment tissue from the end of the left gonial angle (back jaw) to the end of the right gonial angle (back jaw) of an individual. In some embodiments, a mandibular implant disclosed herein is configured to augment tissue from a point laying in a region between the attachment location of the left mandibular osteocutaneous ligament and left gonial angle (back jaw) to a region between the attachment location of the right mandibular osteocutaneous ligament and the right gonial angle (back jaw) of an individual. Thus, a wrap-around or extended mandibular implant can now be used in circumstances encompassing excising the left and right anterior mental fibrous condensation anteriorly and elevating the left and right medial mandibular and mandibulocutaneous ligaments.

A mandibular implant comprises a body having an axial length, a height and a thickness sized and dimensioned to conform to the general shape of a portion of a jawline of a mandible. A body disclosed herein comprises an outer surface (or an anterior-facing surface), an inner surface (or a posterior-facing surface) opposite the top surface, a top and a bottom opposite the top. The outer surface of a body disclosed herein is generally convex or outwardly arched in shape to augment tissue and confer an aesthetically pleasing profile of the augmented tissue once implanted. Similarly, the inner surface of a body disclosed herein is generally shaped to conform to the contours of a mental protuberance region, a mental tubercle region, and a bottom part of a base region of the body of the mandible, or any combination thereof. In some embodiments, a body of a mandibular implant disclosed herein has substantially U-shaped structure comprising a first end region and a second end region.

A body of a mandibular implant disclosed herein has a longer axial length than current off-the-shelf commercially produced extended chin implants. In some embodiments, a body of a mandibular implant disclosed herein can have axial length of, e.g., about 3 mm, about 4 mm, about 5 mm, about 1 cm or longer than current off-the-shelf commercially produced extended chin implants. In some embodiments, a body of a mandibular implant disclosed herein can have axial length of, e.g., at least 3 mm, at least 4 mm, at least 5 mm, at least 1 cm, or longer than current off-the-shelf commercially produced extended chin implants. In some embodiments, a body of a mandibular implant disclosed herein can have axial length of, e.g., about 3 mm to about 5 mm, about 3 mm to about 1 cm, or about 5 mm to about 1 cm, longer than current off-the-shelf commercially produced extended chin implants.

In some embodiments, a body of a mandibular implant disclosed herein can have axial length that extends past an attachment location of a mandibular osteocutaneous ligament by, e.g., about 3 mm, about 4 mm, about 5 mm, about 7.5 mm, about 1 cm, about 1.5 cm about 2 cm, about 2.5 cm, about 3 cm, about 4 cm or about 5 cm. In some embodiments, a body of a mandibular implant disclosed herein can have axial length that extends past an attachment location of a mandibular osteocutaneous ligament by, e.g., at least 3 mm, at least 4 mm, at least 5 mm, at least 7.5 mm, at least 1 cm, at least 1.5 cm at least 2 cm, at least 2.5 cm, at least 3 cm, at least 4 cm or at least 5 cm. In some embodiments, a body of a mandibular implant disclosed herein can have axial length that extends past an attachment location of a mandibular osteocutaneous ligament by, e.g., at most 3 mm, at most 4 mm, at most 5 mm, at most 7.5 mm, at most 1 cm, at most 1.5 cm at most 2 cm, at most 2.5 cm, at most 3 cm, at most 4 cm or at most 5 cm. In some embodiments, a body of a mandibular implant disclosed herein can have axial length that extends past an attachment location of a mandibular osteocutaneous ligament by, e.g., about 3 mm to about 5 mm, about 3 mm to about 1 cm, about 3 mm to about 1.5 cm, about 3 mm to about 2 cm, about 3 mm to about 2.5 cm, about 3 mm to about 3 cm, about 3 mm to about 4 cm, about 3 mm to about 5 cm, about 5 mm to about 1 cm, about 5 mm to about 1.5 cm, about 5 mm to about 2 cm, about 5 mm to about 2.5 cm, about 5 mm to about 3 cm, about 5 mm to about 4 cm, about 5 mm to about 5 cm, about 1 cm to about 1.5 cm, about 1 cm to about 2 cm, about 1 cm to about 2.5 cm, about 1 cm to about 3 cm, about 1 cm to about 4 cm, about 1 cm to about 5 cm, about 1.5 cm to about 2 cm, about 1.5 cm to about 2.5 cm, about 1.5 cm to about 3 cm, about 1.5 cm to about 4 cm, about 1.5 cm to about 5 cm, 2 cm to about 2.5 cm, about 2 cm to about 3 cm, about 2 cm to about 4 cm, about 2 cm to about 5 cm, about 2.5 cm to about 3 cm, about 2.5 cm to about 4 cm, about 2.5 cm to about 5 cm, about 3 cm to about 4 cm, about 3 cm to about 5 cm, or about 4 cm to about 5 cm.

In some embodiments, a body of a mandibular implant disclosed can have axial length of, e.g., about 70%, about 75%, about 80%, about 85%, about 90%, about 95% or about 100% of the jawline from the left end of the jaw to the right end of the jaw. In some embodiments, a body of a mandibular implant disclosed herein can have axial length of, e.g., at least 70%, at least 75%, at least 80%, at least 85%, at least 90%, at least 95% or at least 100% of the jawline from the left end of the jaw to the right end of the jaw. In some embodiments, a body of a mandibular implant disclosed herein can have axial length of, e.g., at most 70%, at most 75%, at most 80%, at most 85%, at most 90%, at most 95% or at most 100% of the jawline from the left end of the jaw to the right end of the jaw. In some embodiments, a body of a mandibular implant disclosed herein can have axial length of, e.g., about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%.

In some embodiments, a body of a mandibular implant disclosed herein can have a height of, e.g., about 2 mm, about 2.5 mm, about 3 mm, about 3.5 cm, about 4 mm, about 4.5 mm, about 5 mm, about 6 mm, about 7 mm, about 8 mm, about 9 mm, about 1 cm, about 1.5 cm, about 2 cm or about 2.5 cm. In some embodiments, a body of a mandibular implant disclosed herein can have a height of, e.g., at least 2 mm, at least 2.5 mm, at least 3 mm, at least 3.5 cm, at least 4 mm, at least 4.5 mm, at least 5 mm, at least 6 mm, at least 7 mm, at least 8 mm, at least 9 mm, at least 1 cm, at least 1.5 cm, at least 2 cm or at least 2.5 cm. In some embodiments, a body of a mandibular implant disclosed herein can have a height of, e.g., at most 2 mm, at most 2.5 mm, at most 3 mm, at most 3.5 cm, at most 4 mm, at most 4.5 mm, at most 5 mm, at most 6 mm, at most 7 mm, at most 8 mm, at most 9 mm, at most 1 cm, at most 1.5 cm, at most 2 cm or at most 2.5 cm. In some embodiments, a body of a mandibular implant disclosed herein can have a height of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 1.5 cm, about 2 mm to about 2 cm, about 2 mm to about 2.5 cm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 6 mm, about 2.5 mm to about 7 mm, about 2.5 mm to about 8 mm, about 2.5 mm to about 9 mm, about 2.5 mm to about 1 cm, about 2.5 mm to about 1.5 cm, about 2.5 mm to about 2 cm, about 2.5 mm to about 2.5 cm, about 3 mm to about 3.5 mm, about 3 mm to about 4 mm, about 3 mm to about 4.5 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 1.5 cm, about 3 mm to about 2 cm, about 3 mm to about 2.5 cm, about 3.5 mm to about 4 mm, about 3.5 mm to about 4.5 mm, about 3.5 mm to about 5 mm, about 3.5 mm to about 6 mm, about 3.5 mm to about 7 mm, about 3.5 mm to about 8 mm, about 3.5 mm to about 9 mm, about 3.5 mm to about 1 cm, about 3.5 mm to about 1.5 cm, about 3.5 mm to about 2 cm, about 3.5 mm to about 2.5 cm, about 4 mm to about 4.5 mm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 1.5 cm, about 4 mm to about 2 cm, about 4 mm to about 2.5 cm, about 4.5 mm to about 5 mm, about 4.5 mm to about 6 mm, about 4.5 mm to about 7 mm, about 4.5 mm to about 8 mm, about 4.5 mm to about 9 mm, about 4.5 mm to about 1 cm, about 4.5 mm to about 1.5 cm, about 4.5 mm to about 2 cm, about 4.5 mm to about 2.5 cm, about 5 mm to about 6 mm, about 5 mm to about 7 mm, about 5 mm to about 8 mm, about 5 mm to about 9 mm, about 5 mm to about 1 cm, about 5 mm to about 1.5 cm, about 5 mm to about 2 cm, about 5 mm to about 2.5 cm, about 7.5 mm to about 1 cm, about 7.5 mm to about 1.5 cm, about 7.5 mm to about 2 cm, about 7.5 mm to about 2.5 cm, about 1 cm to about 1.5 cm, about 1 cm to about 2 cm, about 1 cm to about 2.5 cm, about 1.5 cm to about 2 cm, about 1.5 cm to about 2.5 cm, or about 2 cm to about 2.5 cm.

In some embodiments, a body of a mandibular implant disclosed herein can have a thickness of, e.g., about 2 mm, about 2.5 mm, about 3 mm, about 4 mm, about 4.5 mm, or about 5 mm. In some embodiments, the mental arch can have a length of, e.g., at least 2 mm, at least 2.5 mm, at least 3 mm, at least 4 mm, at least 4.5 mm, or at least 5 mm. In some embodiments, a body of a mandibular implant disclosed herein can have a thickness of, e.g., at most 2 mm, at most 2.5 mm, at most 3 mm, or at most 4 mm, at most 4.5 mm, or at most 5 mm. In some embodiments, a body of a mandibular implant disclosed herein can have a thickness of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3.5 mm to about 4 mm, about 3 mm to about 4.5 mm, about 3.5 mm to about 5 mm, or about 4 mm to about 5 mm.

In some embodiments, any implantable biomaterials and/or any modification of any implant material that alters the softness or pliability of a mandibular implant disclosed herein can be utilized. As such, a mandibular implant disclosed herein can be made of a wide variety of materials, including but not limited to silicone or silicone elastomers, such as SILASTIC®, for example, alone or reinforced by materials such as PTFE, ePTFE, Dacron, Polyester fiber mesh (MERSILENE®), prolene, propylene, polypropylene, polystyrene, high-density porous Polyethylene (MEDPORE®), other thermoplastic materials, or combinations thereof. A mandibular implant disclosed herein could also include a metal or metal alloy, including but not limited to titanium, tungsten, stainless steel, aluminum, nitinol, and the like. In some embodiments, a mandibular implant disclosed herein are formed by injection molding, or any other suitable process.

In some embodiments, a mandibular implant disclosed herein can be composed of a single material or type of material and does not include an outer shell and an inner core of a different material. In some embodiments, a mandibular implant disclosed herein can be a composite of two or more materials or types of material. For example, a composite mandibular implant disclosed herein can comprise a core comprising a first material and one, two, or more outer layers comprising a second material. In some embodiments, a first material is silicone, and a second material is ePTFE. In some embodiments, a composite mandibular implant disclosed herein comprises, e.g., an outer shell that is not made of a plastic material.

In some embodiments, a mandibular implant disclosed herein can include a body that includes a shell having one unitary layer, or a plurality of layers, such as 2, 3, 4, or more layers and filled or configured to be substantially filled with a filler such as a viscous flowable material, and/or a foam. The viscous material can be selected for a combination of non-toxicity as well as to provide structural support to the surrounding tissue while maintaining a natural feel. For example, the viscous material can include saline, water, silicone, silicone gel, a triglyceride oil, a block co-polymer, or other materials. In some embodiments, a mandibular implant disclosed herein can be configured to be filled with any desired volume, such as for example between about 0.5 mL and about 10 mL, or about, at least about, or no more than about 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, or ranges including any two of the foregoing values. The volume can then be synergistically augmented by the excision of one, two, or more structures, e.g., at the periosteal level as described elsewhere herein.

In some embodiments, a mandibular implant disclosed herein has a flexible body that is not rigid to mimic natural body contours, including the chin and is configured such that the surrounding native tissue can move vis-à-vis the implant. In some embodiments, the silicone rubber material durometer, or softness, at the surface of a mandibular implant disclosed herein can range from "A-scale" 70-5, such as about 70, 60 50, 45, 40, 35, 30, 25, 20, 5 or ranges including one or more of the foregoing values, and can range from "00-scale" 50-"000-scale" 10 at the implant center, such that the implant shape is stable.

A mandibular implant disclosed herein can have a smooth or textured surface. In some embodiments, a mandibular implant disclosed herein can promote ingrowth, or inhibit or prevent ingrowth. For example, a mandibular implant disclosed herein can be smooth surfaced, or have a conforming backed posterior surface that uses a serrated backing that reduces the memory of the implant.

In some embodiments, a body of a mandibular implant disclosed herein comprises a mental arch, a left lateral arm, and a right lateral arm. A single-piece implant, left lateral arm extends from the left end of the mental arch while the right lateral arm extends from the right end of the mental arch. A mental arch disclosed herein comprises an outer surface (or an anterior-facing surface), an inner surface (or a posterior-facing surface) opposite the top surface, a top and a bottom opposite the top. Similarly, a left lateral arm disclosed herein comprises an outer surface (or an anterior-facing surface), an inner surface (or a posterior-facing surface) opposite the outer surface, a top and a bottom opposite the top, while a right lateral arm disclosed herein comprises an outer surface (or an anterior-facing surface), an inner surface (or a posterior-facing surface) opposite the outer surface, a top and a bottom opposite the top. The outer surface of the mental arch and left and right lateral arms are contiguous to form a uniform surface, the outer surface generally being convex or outwardly arched in shape to augment tissue and confer an aesthetically pleasing profile of the augmented tissue once implanted. Similarly, the inner surface of the mental arch and left and right lateral arms are contiguous to form a uniform surface. Likewise, the tops of the mental arch and left and right lateral arms form a contiguous edge as do the bottoms of the mental arch and left and right lateral arms. The inner surface of the mental arch and left and right lateral arms are generally shaped to conform to the contours of a mental protuberance region, a mental tubercle region, and a bottom part of a base region of the body of the mandible.

In some embodiments, a mandibular implant disclosed herein is sized and dimension to have a perimeter length of its outer surface from one end to a second end of, e.g., about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm, or about 30 cm and ranges including any two of the foregoing values. In some embodiments, a mandibular implant disclosed herein is sized and dimensioned to have a perimeter length of its outer surface from one end to a second end of, e.g., at least 15 cm, at least 16 cm, at least 17 cm, at least 18 cm, at least 19 cm, at least 20 cm, at least 21 cm, at least 22 cm, at least 23 cm, at least 24 cm, at least 25 cm, at least 26 cm, at least 27 cm, at least 28 cm, at least 29 cm, or at least 30 cm. In some embodiments, a mandibular implant disclosed herein is sized and dimensioned to have a perimeter length of its outer surface from one end to a second end of, e.g., at most 15 cm, at most 16 cm, at most 17 cm, at most 18 cm, at most 19 cm, at most 20 cm, at most 21 cm, at most 22 cm, at most 23 cm, at most 24 cm, at most 25 cm, at most 26 cm, at most 27 cm, at most 28 cm, at most 29 cm, or at most 30 cm. In some embodiments, a mandibular implant disclosed herein is sized and dimensioned to have a perimeter length of its outer surface from one end to a second end of, e.g., about 15 cm to 18 cm, about 15 cm to 20 cm, about 15 cm to 23 cm, about 15 cm to 25 cm, about 15 cm to 28 cm, about 15 cm to 30 cm, about 18 cm to 20 cm, about 18 cm to 23 cm, about 18 cm to 25 cm, about 18 cm to 28 cm, about 18 cm to 30 cm, about 20 cm to 23 cm, about 20 cm to 25 cm, about 20 cm to 28 cm, about 20 cm to 30 cm, about 25 cm to 28 cm, or about 25 cm to 30 cm.

A mental arch disclosed herein has a length, a height, and a thickness sized and dimensioned to conform to the general shape of a mental protuberance region, a mental tubercle region, or any combination thereof. An inner surface of a mental arch is configured to properly seat on the surface of a region of the mental protuberance and left and right mental tubercles (chin) of the mandible. In some embodiments, a mental arch can have a length that extends from the left mental foramen to the right mental foramen. In some embodiments, a mental arch can have a length of, e.g., about 2 cm, about 2.5 cm, about 3 cm, about 3.5 cm, about 4 cm, about 4.5 cm, or about 5 cm. In some embodiments, a mental arch can have a length of, e.g., at least 2 cm, at least 2.5 cm, at least 3 cm, at least 4 cm, at least 4.5 cm, at least 5 cm. In some embodiments, a mental arch can have a length of, e.g., at most 2 cm, at most 2.5 cm, at most 3 cm, at most 4 cm, at most 4.5 cm, at most 5 cm. In some embodiments, a mental arch can have a length of, e.g., about 2 cm to about 2.5 cm, about 2 cm to about 3 cm, about 2 cm to about 3.5 cm, about 2 cm to about 4 cm, about 2 cm to about 4.5 cm, about 2 cm to about 5 cm, about 2.5 cm to about 3 cm, about 2.5 cm to about 3.5 cm, about 2.5 cm to about 4 cm, about 2.5 cm to about 4.5 cm, about 2.5 cm to about 5 cm, about 3 cm to about 3.5 cm, about 3 cm to about 4 cm, about 3 cm to about 4.5 cm, about 3 cm to about 5 cm, about 3.5 cm to about 4 cm, about 3.5 cm to about 4.5 cm, about 3.5 cm to about 5 cm, about 4 cm to about 4.5 cm, about 4 cm to about 5 cm, or about 4.5 cm to about 5 cm.

In some embodiments, a mental arch can have a height of, e.g., about 2 mm, about 2.5 mm, about 3 mm, about 3.5 cm, about 4 mm, about 4.5 mm, about 5 mm, about 6 mm, about 7 mm, about 8 mm, about 9 mm, about 1 cm, about 1.5 cm, about 2 cm or about 2.5 cm. In some embodiments, a mental arch can have a height of, e.g., at least 2 mm, at least 2.5 mm, at least 3 mm, at least 3.5 cm, at least 4 mm, at least 4.5 mm, at least 5 mm, at least 6 mm, at least 7 mm, at least 8 mm, at least 9 mm, at least 1 cm, at least 1.5 cm, at least 2 cm or at least 2.5 cm. In some embodiments, a mental arch can have a height of, e.g., at most 2 mm, at most 2.5 mm, at most 3 mm, at most 3.5 cm, at most 4 mm, at most 4.5 mm, at most 5 mm, at most 6 mm, at most 7 mm, at most 8 mm, at most 9 mm, at most 1 cm, at most 1.5 cm, at most 2 cm or at most 2.5 cm. In some embodiments, a mental arch can have a height of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 1.5 cm, about 2 mm to about 2 cm, about 2 mm to about 2.5 cm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 6 mm, about 2.5 mm to about 7 mm, about 2.5 mm to about 8 mm, about 2.5 mm to about 9 mm, about 2.5 mm to about 1 cm, about 2.5 mm to about 1.5 cm, about 2.5 mm to about 2 cm, about 2.5 mm to about 2.5 cm, about 3 mm to about 3.5 mm, about 3 mm to about 4 mm, about 3 mm to about 4.5 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 1.5 cm, about 3 mm to about 2 cm, about 3 mm to about 2.5 cm, about 3.5 mm to about 4 mm, about 3.5 mm to about 4.5 mm, about 3.5 mm to about 5 mm, about 3.5 mm to about 6 mm, about 3.5 mm to about 7 mm, about 3.5 mm to about 8 mm, about 3.5 mm to about 9 mm, about 3.5 mm to about 1 cm, about 3.5 mm to about 1.5 cm, about 3.5 mm to about 2 cm, about 3.5 mm to about 2.5 cm, about 4 mm to about 4.5 mm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 1.5 cm, about 4 mm to about 2 cm, about 4 mm to about 2.5 cm, about 4.5 mm to about 5 mm, about 4.5 mm to about 6 mm, about 4.5 mm to about 7 mm, about 4.5 mm to about 8 mm, about 4.5 mm to about 9 mm, about 4.5 mm to about 1 cm, about 4.5 mm to about 1.5 cm, about 4.5 mm to about 2 cm, about 4.5 mm to about 2.5 cm, about 5 mm to about 6 mm, about 5 mm to about 7 mm, about 5 mm to about 8 mm, about 5 mm to about 9 mm, about 5 mm to about 1 cm, about 5 mm to about 1.5 cm, about 5 mm to about 2 cm, about 5 mm to about 2.5 cm, about 7.5 mm to about 1 cm, about 7.5 mm to about 1.5 cm, about 7.5 mm to about 2 cm, about 7.5 mm to about 2.5 cm, about 1 cm to about 1.5 cm, about 1 cm to about 2 cm, about 1 cm to about 2.5 cm, about 1.5 cm to about 2 cm, about 1.5 cm to about 2.5 cm, or about 2 cm to about 2.5 cm.

In some embodiments, a mental arch can have a thickness of, e.g., about 2 mm, about 2.5 mm, about 3 mm, about 4 mm, about 4.5 mm, or about 5 mm. In some embodiments, the mental arch can have a length of, e.g., at least 2 mm, at least 2.5 mm, at least 3 mm, at least 4 mm, at least 4.5 mm, or at least 5 mm. In some embodiments, a mental arch can have a thickness of, e.g., at most 2 mm, at most 2.5 mm, at most 3 mm, or at most 4 mm, at most 4.5 mm, or at most 5 mm. In some embodiments, a mental arch can have a thickness of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3.5 mm to about 4 mm, about 3 mm to about 4.5 mm, about 3.5 mm to about 5 mm, or about 4 mm to about 5 mm.

Left and right lateral arms each have a length, height and thickness and each is sized and dimensioned to conform to the general shape of the bottom portion or base of the body of the mandible. An inner surface of a left lateral arm is configured to properly seat on the surface of the left base of the mandibular body while inner surface of a right lateral arm is configured to properly seat on the surface of the right base of the mandibular body.

In some embodiments, left and right lateral arms can each independently have a length that extends past the attachment location of their respective left and right mandibular osteocutaneous ligaments. In some embodiments, left and right lateral arms can each independently have a length that extends, e.g., about 1 cm, about 1.5 cm, about 2 cm, about 2.5 cm, about 3 cm, about 3.5 cm, or about 4 cm past the attachment location of their respective left and right mandibular osteocutaneous ligaments. In some embodiments, a left and a right lateral arm can each independently have a length that extends, e.g., at least 1 cm, at least 1.5 cm, at least 2 cm, at least 2.5 cm, at least 3 cm, at least 3.5 cm, or at least 4 cm past the attachment location of their respective left and right mandibular osteocutaneous ligaments. In some embodiments, a left and a right lateral arm can each independently have a length that extends, e.g., at most 1 cm, at most 1.5 cm, at most 2 cm, at most 2.5 cm, at most 3 cm, at most 3.5 cm, or at most 4 cm past the attachment location of their respective left and right mandibular osteocutaneous ligaments. In some embodiments, a left and a right lateral arm can each independently have a length that extends, e.g., about 1 cm to about 1.5 cm, about 1 cm to about 2 cm, about 1 cm to about 2.5 cm, about 1 cm to about 3 cm, about 1 cm to about 3.5 cm, about 1 cm to about 4 cm, about 2 cm to about 3 cm, bout 2 cm to about 3.5 cm, about 2 cm to about 4 cm, about 3 cm to about 3.5 cm, about 3 cm to about 4 cm, or about 3.5 cm to about 4 cm, past the attachment location of their respective left and right mandibular osteocutaneous ligaments. In some embodiments, a left and a right lateral arm can each independently have a length that extend all the way to the gonial angle of the mandible.

In some embodiments, a left and a right lateral arm can each independently have a length of, e.g., about 2 cm, about 2.5 cm, about 3 cm, about 3.5 cm, about 4 cm, about 4.5 cm, or about 5 cm. In some embodiments, a left and a right lateral arm can each independently have a length of, e.g., at least 2 cm, at least 2.5 cm, at least 3 cm, at least 4 cm, at least 4.5 cm, at least 5 cm. In some embodiments, a left and a right lateral arm can each independently have a length of, e.g., at most 2 cm, at most 2.5 cm, at most 3 cm, at most 4 cm, at most 4.5 cm, at most 5 cm. In some embodiments, a left and a right lateral arm can each independently have a length of, e.g., about 2 cm to about 2.5 cm, about 2 cm to about 3 cm, about 2 cm to about 3.5 cm, about 2 cm to about 4 cm, about 2 cm to about 4.5 cm, about 2 cm to about 5 cm, about 2.5 cm to about 3 cm, about 2.5 cm to about 3.5 cm, about 2.5 cm to about 4 cm, about 2.5 cm to about 4.5 cm, about 2.5 cm to about 5 cm, about 3 cm to about 3.5 cm, about 3 cm to about 4 cm, about 3 cm to about 4.5 cm, about 3 cm to about 5 cm, about 3.5 cm to about 4 cm, about 3.5 cm to about 4.5 cm, about 3.5 cm to about 5 cm, about 4 cm to about 4.5 cm, about 4 cm to about 5 cm, or about 4.5 cm to about 5 cm.

In some embodiments, a left and a right lateral arm can each independently have a height of, e.g., about 2 mm, about 2.5 mm, about 3 mm, about 3.5 cm, about 4 mm, about 4.5 mm, about 5 mm, about 6 mm, about 7 mm, about 8 mm, about 9 mm, about 1 cm, about 1.5 cm, about 2 cm or about 2.5 cm. In some embodiments, a left and a right lateral arm can each independently have a height of, e.g., at least 2 mm, at least 2.5 mm, at least 3 mm, at least 3.5 cm, at least 4 mm, at least 4.5 mm, at least 5 mm, at least 6 mm, at least 7 mm, at least 8 mm, at least 9 mm, at least 1 cm, at least 1.5 cm, at least 2 cm or at least 2.5 cm. In some embodiments, a left and a right lateral arm can each independently have a height of, e.g., at most 2 mm, at most 2.5 mm, at most 3 mm, at most 3.5 cm, at most 4 mm, at most 4.5 mm, at most 5 mm, at most 6 mm, at most 7 mm, at most 8 mm, at most 9 mm, at most 1 cm, at most 1.5 cm, at most 2 cm or at most 2.5 cm. In some embodiments, a left and a right lateral arm can each independently have a height of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 1.5 cm, about 2 mm to about 2 cm, about 2 mm to about 2.5 cm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 6 mm, about 2.5 mm to about 7 mm, about 2.5 mm to about 8 mm, about 2.5 mm to about 9 mm, about 2.5 mm to about 1 cm, about 2.5 mm to about 1.5 cm, about 2.5 mm to about 2 cm, about 2.5 mm to about 2.5 cm, about 3 mm to about 3.5 mm, about 3 mm to about 4 mm, about 3 mm to about 4.5 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 1.5 cm, about 3 mm to about 2 cm, about 3 mm to about 2.5 cm, about 3.5 mm to about 4 mm, about 3.5 mm to about 4.5 mm, about 3.5 mm to about 5 mm, about 3.5 mm to about 6 mm, about 3.5 mm to about 7 mm, about 3.5 mm to about 8 mm, about 3.5 mm to about 9 mm, about 3.5 mm to about 1 cm, about 3.5 mm to about 1.5 cm, about 3.5 mm to about 2 cm, about 3.5 mm to about 2.5 cm, about 4 mm to about 4.5 mm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 1.5 cm, about 4 mm to about 2 cm, about 4 mm to about 2.5 cm, about 4.5 mm to about 5 mm, about 4.5 mm to about 6 mm, about 4.5 mm to about 7 mm, about 4.5 mm to about 8 mm, about 4.5 mm to about 9 mm, about 4.5 mm to about 1 cm, about 4.5 mm to about 1.5 cm, about 4.5 mm to about 2 cm, about 4.5 mm to about 2.5 cm, about 5 mm to about 6 mm, about 5 mm to about 7 mm, about 5 mm to about 8 mm, about 5 mm to about 9 mm, about 5 mm to about 1 cm, about 5 mm to about 1.5 cm, about 5 mm to about 2 cm, about 5 mm to about 2.5 cm, about 7.5 mm to about 1 cm, about 7.5 mm to about 1.5 cm, about 7.5 mm to about 2 cm, about 7.5 mm to about 2.5 cm, about 1 cm to about 1.5 cm, about 1 cm to about 2 cm, about 1 cm to about 2.5 cm, about 1.5 cm to about 2 cm, about 1.5 cm to about 2.5 cm, or about 2 cm to about 2.5 cm.

In some embodiments, a left and a right lateral arm can each independently have a thickness of, e.g., about 2 mm, about 2.5 mm, about 3 mm, about 4 mm, about 4.5 mm, or about 5 mm. In some embodiments, a left and a right lateral arm can each independently have a thickness of, e.g., at least 2 mm, at least 2.5 mm, at least 3 mm, at least 4 mm, at least 4.5 mm, or at least 5 mm. In some embodiments, a left and a right lateral arm can each independently have a thickness of, e.g., at most 2 mm, at most 2.5 mm, at most 3 mm, or at most 4 mm, at most 4.5 mm, or at most 5 mm. In some embodiments, a left and a right lateral arm can each independently have a thickness of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3.5 mm to about 4 mm, about 3 mm to about 4.5 mm, about 3.5 mm to about 5 mm, or about 4 mm to about 5 mm.

In some embodiments, the size and dimension of a left and a right lateral arm is independently shaped to impart a full jawline enhancement, with the length of each arm gradually tapering in height and thickness in a direction toward the end of each arm. In some embodiments, the size and dimension of a left and a right lateral arm is independently shaped to impart a full jawline enhancement, with the length of each arm tapering in height and thickness in a direction toward the end of each arm. In some embodiments, a left and a right lateral arm is independently tapered from a height of about 3 mm to about 6 mm from the border of the mental arch to a height of about 2 mm to about 4 mm at the lateral end of the arm and independently tapered from a thickness of about 3 mm to about 5 mm from the border of the mental arch to a height of about 2 mm to about 4 mm at the lateral end of the arm.

In some embodiments, the size and dimension of a left and a right lateral arm is independently shaped to impart a narrow jawline enhancement, with the length of each arm tapering in height and thickness in a direction toward the end of each arm. In some embodiments, a left and a right lateral arm is independently tapered from a height of about 2 mm to about 4 mm from the border of the mental arch to a height of about 1 mm to about 2 mm at the lateral end of the arm and independently tapered from a thickness of about 2 mm to about 3 mm from the border of the mental arch to a height of about 1 mm to about 2 mm at the lateral end of the arm.

In some embodiments, the size and dimension of a left and a right lateral arm is independently shaped to impart a expanded jawline enhancement, with the length of each arm increasing in height and thickness in a direction toward the end of each arm. In some embodiments, a left and a right lateral arm is independently increased from a height of about 3 mm to about 5 mm from the border of the mental arch to a height of about 4 mm to about 6 mm at the lateral end of the arm and independently increased from a thickness of about 1 mm to about 3 mm from the border of the mental arch to a height of about 2 mm to about 4 mm at the lateral end of the arm.

In some embodiments, left and right lateral arms can each independently have one or more protrusions or lateral projections located on the outer surface. Protrusions are lateral bumps extending radially outward from the outer surface of a lateral arm and each is configured to fill in and smooth out soft tissue defects on the side of the jaw and provide an aesthetic enhancement to the jawline. Positioning of a protrusion on a left or right lateral arm can vary in location depending on the desired anatomical effect. In some embodiments, a left and a right lateral arm each independently has protrusion with each protrusion sized and dimensioned identically or substantially similar to each other. In some embodiments, a left and a right lateral arm each independently has protrusion with each protrusion sized and dimensioned identically or substantially similar to each other, are symmetrically positioned on left and right lateral arms. In some embodiments, a left and a right lateral arm each independently has two protrusions with each protrusion sized and dimensioned identically or substantially similar to each other. In some embodiments, a left and a right lateral arm each independently has two protrusions with each protrusion sized and dimensioned identically or substantially similar to each other, are symmetrically positioned on left and right lateral arms.

A protrusion can have a length, height and thickness and each is sized and dimensioned to augment tissue and confer an aesthetically pleasing profile of the augmented tissue once implanted. In some embodiments, a protrusion can have a length of, e.g., about 0.5 cm, about 0.75 cm, about 1 cm, about 1.5 cm, about 2 cm, about 2.5 cm, about 3 cm, about 3.5 cm, about 4 cm, about 4.5 cm, or about 5 cm, or ranges including any two of the foregoing values. In some embodiments, a protrusion can have a length of, e.g., at least 0.5 cm, at least 0.75 cm, at least 1 cm, at least 1.5 cm, at least 2 cm, at least 2.5 cm, at least 3 cm, at least 3.5 cm, at least 4 cm, at least 4.5 cm, or at least 5 cm. In some embodiments, a protrusion can have a length of, e.g., at most 0.5 cm, at most 0.75 cm, at most 1 cm, at most 1.5 cm, at most 2 cm, at most 2.5 cm, at most 3 cm, at most 3.5 cm, at most 4 cm, at most 4.5 cm, or at most 5 cm.

In some embodiments, a protrusion can have a length of, e.g., about 0.5 cm about 0.75 cm, about 0.5 cm to about 1 cm, about 0.5 cm to about 1.5 cm, about 0.5 cm to about 2 cm, about 0.5 cm to about 2.5 cm, about 0.5 cm to about 3 cm, about 0.5 cm to about 3.5 cm, about 0.5 cm to about 4 cm, about 0.5 cm to about 4.5 cm, about 0.5 cm to about 5 cm, about 0.75 cm to about 1.5 cm, about 0.75 cm to about 2 cm, about 0.75 cm to about 2.5 cm, about 0.75 cm to about 3 cm, about 0.75 cm to about 3.5 cm, about 0.75 cm to about 4 cm, about 0.75 cm to about 4.5 cm, about 0.75 cm to about 5 cm, about 1 cm to about 1.5 cm, about 1 cm to about 2 cm, about 1 cm to about 2.5 cm, about 1 cm to about 3 cm, about 1 cm to about 3.5 cm, about 1 cm to about 4 cm, about 1 cm to about 4.5 cm, about 1 cm to about 5 cm, about 1.5 cm to about 2 cm, about 1.5 cm to about 2.5 cm, about 1.5 cm to about 3 cm, about 1.5 cm to about 3.5 cm, about 1.5 cm to about 4 cm, about 1.5 cm to about 4.5 cm, about 1.5 cm to about 5 cm, about 2 cm to about 2.5 cm, about 2 cm to about 3 cm, about 2 cm to about 3.5 cm, about 2 cm to about 4 cm, about 2 cm to about 4.5 cm, about 2 cm to about 5 cm, about 2.5 cm to about 3 cm, about 2.5 cm to about 3.5 cm, about 2.5 cm to about 4 cm, about 2.5 cm to about 4.5 cm, about 2.5 cm to about 5 cm, about 3 cm to about 3.5 cm, about 3 cm to about 4 cm, about 3 cm to about 4.5 cm, about 3 cm to about 5 cm, about 3.5 cm to about 4 cm, about 3.5 cm to about 4.5 cm, about 3.5 cm to about 5 cm, about 4 cm to about 4.5 cm, about 4 cm to about 5 cm, or about 4.5 cm to about 5 cm.

In some embodiments, a protrusion can have a height of, e.g., about 2 mm, about 2.5 mm, about 3 mm, about 3.5 cm, about 4 mm, about 4.5 mm, about 5 mm, about 6 mm, about 7 mm, about 8 mm, about 9 mm, about 1 cm, about 1.5 cm, about 2 cm or about 2.5 cm. In some embodiments, a protrusion can have a height of, e.g., at least 2 mm, at least 2.5 mm, at least 3 mm, at least 3.5 cm, at least 4 mm, at least 4.5 mm, at least 5 mm, at least 6 mm, at least 7 mm, at least 8 mm, at least 9 mm, at least 1 cm, at least 1.5 cm, at least 2 cm or at least 2.5 cm. In some embodiments, a protrusion can have a height of, e.g., at most 2 mm, at most 2.5 mm, at most 3 mm, at most 3.5 cm, at most 4 mm, at most 4.5 mm, at most 5 mm, at most 6 mm, at most 7 mm, at most 8 mm, at most 9 mm, at most 1 cm, at most 1.5 cm, at most 2 cm or at most 2.5 cm. In some embodiments, a protrusion can have a height of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 1.5 cm, about 2 mm to about 2 cm, about 2 mm to about 2.5 cm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 6 mm, about 2.5 mm to about 7 mm, about 2.5 mm to about 8 mm, about 2.5 mm to about 9 mm, about 2.5 mm to about 1 cm, about 2.5 mm to about 1.5 cm, about 2.5 mm to about 2 cm, about 2.5 mm to about 2.5 cm, about 3 mm to about 3.5 mm, about 3 mm to about 4 mm, about 3 mm to about 4.5 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 1.5 cm, about 3 mm to about 2 cm, about 3 mm to about 2.5 cm, about 3.5 mm to about 4 mm, about 3.5 mm to about 4.5 mm, about 3.5 mm to about 5 mm, about 3.5 mm to about 6 mm, about 3.5 mm to about 7 mm, about 3.5 mm to about 8 mm, about 3.5 mm to about 9 mm, about 3.5 mm to about 1 cm, about 3.5 mm to about 1.5 cm, about 3.5 mm to about 2 cm, about 3.5 mm to about 2.5 cm, about 4 mm to about 4.5 mm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 1.5 cm, about 4 mm to about 2 cm, about 4 mm to about 2.5 cm, about 4.5 mm to about 5 mm, about 4.5 mm to about 6 mm, about 4.5 mm to about 7 mm, about 4.5 mm to about 8 mm, about 4.5 mm to about 9 mm, about 4.5 mm to about 1 cm, about 4.5 mm to about 1.5 cm, about 4.5 mm to about 2 cm, about 4.5 mm to about 2.5 cm, about 5 mm to about 6 mm, about 5 mm to about 7 mm, about 5 mm to about 8 mm, about 5 mm to about 9 mm, about 5 mm to about 1 cm, about 5 mm to about 1.5 cm, about 5 mm to about 2 cm, about 5 mm to about 2.5 cm, about 7.5 mm to about 1 cm, about 7.5 mm to about 1.5 cm, about 7.5 mm to about 2 cm, about 7.5 mm to about 2.5 cm, about 1 cm to about 1.5 cm, about 1 cm to about 2 cm, about 1 cm to about 2.5 cm, about 1.5 cm to about 2 cm, about 1.5 cm to about 2.5 cm, or about 2 cm to about 2.5 cm.

In some embodiments, a protrusion extends radially outward from an outer surface of a lateral arm and can have a thickness of, e.g., about 1 mm, about 2 mm, about 3 mm, about 4 mm, about 5 mm, about 6 mm, about 7 mm, about 8 mm, about 9 mm, about 1 cm, about 1.5 cm, about 2 cm, about 2.5 cm, or about 3 cm, or ranges including any two of the foregoing values. In some embodiments, a protrusion extends radially outward from an outer surface of a lateral arm and can have a thickness of, e.g., at least 1 mm, at least 2 mm, at least 3 mm, at least 4 mm, at least 5 mm, at least 6 mm, at least 7 mm, at least 8 mm, at least 9 mm, at least 1 cm, at least 1.5 cm, at least 2 cm, at least 2.5 cm, or at least 3 cm. In some embodiments, a protrusion extends radially outward from an outer surface of a lateral arm and can have a thickness of, e.g., at most 1 mm, at most 2 mm, at most 3 mm, at most 4 mm, at most 5 mm, at most 6 mm, at most 7 mm, at most 8 mm, at most 9 mm, at most 1 cm, at most 1.5 cm, at most 2 cm, at most 2.5 cm, or at most 3 cm. In some embodiments, a protrusion extends radially outward from an outer surface of a lateral arm and can have a thickness of, e.g., about 1 mm to about 2.5 mm, about 1 mm to about 5 mm, about 1 mm to about 7.5 mm, about 1 mm to about 1 cm, about 1 mm to about 1.5 cm, about 1 mm to about 2 cm, about 1 mm to about 2.5 cm, about 1 mm to about 3 cm, about 2 mm to about 3 mm, about 2.5 mm to about 5 mm, about 2.5 mm to about 7.5 mm, about 2.5 mm to about 1 cm, about 2.5 mm to about 1.5 cm, about 2.5 mm to about 2 cm, about 2.5 mm to about 2.5 cm, about 2.5 mm to about 3 cm, about 5 mm to about 7.5 mm, about 5 mm to about 1 cm, about 5 mm to about 1.5 cm, about 5 mm to about 2 cm, about 5 mm to about 2.5 cm, about 5 mm to about 3 cm, about 7.5 mm to about 1 cm, about 7.5 mm to about 1.5 cm, about 7.5 mm to about 2 cm, about 7.5 mm to about 2.5 cm, about 7.5 mm to about 3 cm, about 1 cm to about 1.5 cm, about 1 cm to about 2 cm, about 1 cm to about 2.5 cm, about 1 cm to about 3 cm, about 1.5 cm to about 2 cm, about 1.5 cm to about 2.5 cm, about 1.5 cm to about 3 cm, about 2 cm to about 2.5 cm, about 2 cm to about 3 cm, or about 2.5 cm to about 3 cm.

In some embodiments, left and right lateral arms can each independently have a ramus extension projecting superiorly from the top edge of their respective lateral end. A ramus extension forms a discrete back jaw component that provides a mandibular angle augmentation or enhancement. A ramus extension disclosed herein has a length, a height, and a thickness and is sized and dimensioned to conform to the general shape of a portion of the ramus of the mandible for which it is designed to provide an aesthetic enhancement to the jaw. Additionally, an inner surface of a ramus extension is generally shaped to conform to the contours of the ramus region of the mandible in order to properly seat on the surface of the ramus.

In some embodiments, a ramus extension can have a length of, e.g., about 2 mm, about 2.5 mm, about 3 mm, about 3.5 cm, about 4 mm, about 4.5 mm, about 5 mm, about 6 mm, about 7 mm, about 8 mm, about 9 mm, about 1 cm, about 1.5 cm, about 2 cm or about 2.5 cm. In some embodiments, a ramus extension can have a length of, e.g., at least 2 mm, at least 2.5 mm, at least 3 mm, at least 3.5 cm, at least 4 mm, at least 4.5 mm, at least 5 mm, at least 6 mm, at least 7 mm, at least 8 mm, at least 9 mm, at least 1 cm, at least 1.5 cm, at least 2 cm or at least 2.5 cm. In some embodiments, a ramus extension can have a length of, e.g., at most 2 mm, at most 2.5 mm, at most 3 mm, at most 3.5 cm, at most 4 mm, at most 4.5 mm, at most 5 mm, at most 6 mm, at most 7 mm, at most 8 mm, at most 9 mm, at most 1 cm, at most 1.5 cm, at most 2 cm or at most 2.5 cm. In some embodiments, a ramus extension can have a length of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 1.5 cm, about 2 mm to about 2 cm, about 2 mm to about 2.5 cm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 6 mm, about 2.5 mm to about 7 mm, about 2.5 mm to about 8 mm, about 2.5 mm to about 9 mm, about 2.5 mm to about 1 cm, about 2.5 mm to about 1.5 cm, about 2.5 mm to about 2 cm, about 2.5 mm to about 2.5 cm, about 3 mm to about 3.5 mm, about 3 mm to about 4 mm, about 3 mm to about 4.5 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 1.5 cm, about 3 mm to about 2 cm, about 3 mm to about 2.5 cm, about 3.5 mm to about 4 mm, about 3.5 mm to about 4.5 mm, about 3.5 mm to about 5 mm, about 3.5 mm to about 6 mm, about 3.5 mm to about 7 mm, about 3.5 mm to about 8 mm, about 3.5 mm to about 9 mm, about 3.5 mm to about 1 cm, about 3.5 mm to about 1.5 cm, about 3.5 mm to about 2 cm, about 3.5 mm to about 2.5 cm, about 4 mm to about 4.5 mm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 1.5 cm, about 4 mm to about 2 cm, about 4 mm to about 2.5 cm, about 4.5 mm to about 5 mm, about 4.5 mm to about 6 mm, about 4.5 mm to about 7 mm, about 4.5 mm to about 8 mm, about 4.5 mm to about 9 mm, about 4.5 mm to about 1 cm, about 4.5 mm to about 1.5 cm, about 4.5 mm to about 2 cm, about 4.5 mm to about 2.5 cm, about 5 mm to about 6 mm, about 5 mm to about 7 mm, about 5 mm to about 8 mm, about 5 mm to about 9 mm, about 5 mm to about 1 cm, about 5 mm to about 1.5 cm, about 5 mm to about 2 cm, about 5 mm to about 2.5 cm, about 7.5 mm to about 1 cm, about 7.5 mm to about 1.5 cm, about 7.5 mm to about 2 cm, about 7.5 mm to about 2.5 cm, about 1 cm to about 1.5 cm, about 1 cm to about 2 cm, about 1 cm to about 2.5 cm, about 1.5 cm to about 2 cm, about 1.5 cm to about 2.5 cm, or about 2 cm to about 2.5 cm.

In some embodiments, a ramus extension can have a height of, e.g., about 2 mm, about 2.5 mm, about 3 mm, about 3.5 cm, about 4 mm, about 4.5 mm, about 5 mm, about 6 mm, about 7 mm, about 8 mm, about 9 mm, about 1 cm, about 1.5 cm, about 2 cm or about 2.5 cm. In some embodiments, a ramus extension can have a height of, e.g., at least 2 mm, at least 2.5 mm, at least 3 mm, at least 3.5 cm, at least 4 mm, at least 4.5 mm, at least 5 mm, at least 6 mm, at least 7 mm, at least 8 mm, at least 9 mm, at least 1 cm, at least 1.5 cm, at least 2 cm or at least 2.5 cm. In some embodiments, a ramus extension can have a height of, e.g., at most 2 mm, at most 2.5 mm, at most 3 mm, at most 3.5 cm, at most 4 mm, at most 4.5 mm, at most 5 mm, at most 6 mm, at most 7 mm, at most 8 mm, at most 9 mm, at most 1 cm, at most 1.5 cm, at most 2 cm or at most 2.5 cm. In some embodiments, a ramus extension can have a height of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 1.5 cm, about 2 mm to about 2 cm, about 2 mm to about 2.5 cm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 6 mm, about 2.5 mm to about 7 mm, about 2.5 mm to about 8 mm, about 2.5 mm to about 9 mm, about 2.5 mm to about 1 cm, about 2.5 mm to about 1.5 cm, about 2.5 mm to about 2 cm, about 2.5 mm to about 2.5 cm, about 3 mm to about 3.5 mm, about 3 mm to about 4 mm, about 3 mm to about 4.5 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 1.5 cm, about 3 mm to about 2 cm, about 3 mm to about 2.5 cm, about 3.5 mm to about 4 mm, about 3.5 mm to about 4.5 mm, about 3.5 mm to about 5 mm, about 3.5 mm to about 6 mm, about 3.5 mm to about 7 mm, about 3.5 mm to about 8 mm, about 3.5 mm to about 9 mm, about 3.5 mm to about 1 cm, about 3.5 mm to about 1.5 cm, about 3.5 mm to about 2 cm, about 3.5 mm to about 2.5 cm, about 4 mm to about 4.5 mm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 1.5 cm, about 4 mm to about 2 cm, about 4 mm to about 2.5 cm, about 4.5 mm to about 5 mm, about 4.5 mm to about 6 mm, about 4.5 mm to about 7 mm, about 4.5 mm to about 8 mm, about 4.5 mm to about 9 mm, about 4.5 mm to about 1 cm, about 4.5 mm to about 1.5 cm, about 4.5 mm to about 2 cm, about 4.5 mm to about 2.5 cm, about 5 mm to about 6 mm, about 5 mm to about 7 mm, about 5 mm to about 8 mm, about 5 mm to about 9 mm, about 5 mm to about 1 cm, about 5 mm to about 1.5 cm, about 5 mm to about 2 cm, about 5 mm to about 2.5 cm, about 7.5 mm to about 1 cm, about 7.5 mm to about 1.5 cm, about 7.5 mm to about 2 cm, about 7.5 mm to about 2.5 cm, about 1 cm to about 1.5 cm, about 1 cm to about 2 cm, about 1 cm to about 2.5 cm, about 1.5 cm to about 2 cm, about 1.5 cm to about 2.5 cm, or about 2 cm to about 2.5 cm.

In some embodiments, a ramus extension can have a thickness of, e.g., about 2 mm, about 2.5 mm, about 3 mm, about 4 mm, about 4.5 mm, or about 5 mm. In some embodiments, the mental arch can have a length of, e.g., at least 2 mm, at least 2.5 mm, at least 3 mm, at least 4 mm, at least 4.5 mm, or at least 5 mm. In some embodiments, a ramus extension can have a thickness of, e.g., at most 2 mm, at most 2.5 mm, at most 3 mm, or at most 4 mm, at most 4.5 mm, or at most 5 mm. In some embodiments, a ramus extension can have a thickness of, e.g., about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3.5 mm to about 4 mm, about 3 mm to about 4.5 mm, about 3.5 mm to about 5 mm, or about 4 mm to about 5 mm.

In some embodiments, a mandibular implant disclosed herein can have one or more tabs projecting posteriorly from the bottom edge of the inner surface of the mental arch, left lateral arm, right lateral arm, or any combination thereof. A tab disclosed herein is configured to fit underneath the edge of a portion of the mandible in order to secure proper placement of a mandibular implant disclosed herein. A tab disclosed herein increase stability of mandibular implant, prevent fibrous attachment to the mandible, as well as provide a smooth transition between different or adjacent areas of the mandible. A tab disclosed herein can be integrally formed with, or separately attached to the inner surface of a mandibular implant disclosed herein, and be made of the same or a different material from the implant. Non-limiting examples of a tab include a base tab, a submental tab, and an extended tab which cover the submental and a portion of the base of the mandibular body.

In some embodiments, a mandibular implant disclosed herein can have one tab projecting posteriorly from the bottom edge of the inner surface of the mental arch, left lateral arm, right lateral arm, or any combination thereof. In some embodiments, a mandibular implant disclosed herein can have a plurality of tabs projecting posteriorly from the bottom edge of the inner surface of the mental arch, left lateral arm, right lateral arm, or any combination thereof. In aspects of these embodiments, a mandibular implant disclosed herein can have 2, 3, 4, 5, 6, 7, or 8 tabs projecting posteriorly from the bottom edge of the inner surface of the mental arch, left lateral arm, right lateral arm, or any combination thereof. In other aspects of these embodiments, a mandibular implant disclosed herein can have at least 2, at least 3, at least 4, at least 5, at least 6, at least 7, or at least 8 tabs projecting posteriorly from the bottom edge of the inner surface of the mental arch, left lateral arm, right lateral arm, or any combination thereof. In yet other aspects of these embodiments, a mandibular implant disclosed herein can have at most 2, at most 3, at most 4, at most 5, at most 6, at most 7, or at most 8 tabs projecting posteriorly from the bottom edge of the inner surface of the mental arch, left lateral arm, right lateral arm, or any combination thereof. In aspects of these embodiments, a mandibular implant disclosed herein can have 2 to 3, 2 to 4, 2 to 5, 2 to 6, 2 to 7, 2 to 8, 3 to 4, 3 to 5, 3 to 6, 3 to 7, 3 to 8, 4 to 5, 4 to 6, 4 to 7, 4 to 8, 5 to 6, 5 to 7, 5 to 8, 6 to 7, 6 to 8, or 7 to 8 tabs projecting posteriorly from the bottom edge of the inner surface of the mental arch, left lateral arm, right lateral arm, or any combination thereof. When more than one tab is present, the tabs are laterally but not necessarily evenly spaced-apart along the bottom edge of the inner surface of the portion of the mandibular implant.

A tab disclosed herein has a length, a height, and a thickness and is sized and dimensioned to provide a securing fit to the underneath edge of a portion of the mandible in order to secure proper placement of a mandibular implant disclosed herein. In some embodiments, a tab disclosed herein can have a length of, e.g., about 2 mm, about 3 mm, about 4 mm, about 5 mm, about 6 mm, about 7 mm, about 8 mm, about 9 mm, about 1 cm, about 1.5 cm, about 2 cm, about 3 cm, about 4 cm, about 5 cm, or about 6 cm. In some embodiments, a tab disclosed herein can have a length of, e.g., at least 2 mm, at least 3 mm, at least 4 mm, at least 5 mm, at least 6 mm, at least 7 mm, at least 8 mm, at least 9 mm, at least 1 cm, at least 1.5 cm, at least 2 cm, at least 3 cm, at least 4 cm, at least 5 cm, or at least 6 cm. In some embodiments, a tab disclosed herein can have a length of, e.g., at most 2 mm, at most 3 mm, at most 4 mm, at most 5 mm, at most 6 mm, at most 7 mm, at most 8 mm, at most 9 mm, at most 1 cm, at most 1.5 cm, at most 2 cm, at most 3 cm, at most 4 cm, at most 5 cm, or at most 6 cm.

In some embodiments, a tab disclosed herein can have a length of, e.g., about 2 m to about 3 mm, about 2 mm to about 4 mm, about 2 mm to about 5 mm, about 2 mm to about 6 mm, about 2 mm to about 7 mm, about 2 mm to about 8 mm, about 2 mm to about 9 mm, about 2 mm to about 1 cm, about 2 mm to about 2 cm, about 2 mm to about 3 cm, about 2 mm to about 4 cm, about 2 mm to about 5 cm, about 2 mm to about 6 cm, about 3 mm to about 4 mm, about 3 mm to about 5 mm, about 3 mm to about 6 mm, about 3 mm to about 7 mm, about 3 mm to about 8 mm, about 3 mm to about 9 mm, about 3 mm to about 1 cm, about 3 mm to about 2 cm, about 3 mm to about 3 cm, about 3 mm to about 4 cm, about 3 mm to about 5 cm, about 3 mm to about 6 cm, about 4 mm to about 5 mm, about 4 mm to about 6 mm, about 4 mm to about 7 mm, about 4 mm to about 8 mm, about 4 mm to about 9 mm, about 4 mm to about 1 cm, about 4 mm to about 2 cm, about 4 mm to about 3 cm, about 4 mm to about 4 cm, about 4 mm to about 5 cm, about 4 mm to about 6 cm, about 5 mm to about 6 mm, about 5 mm to about 7 mm, about 5 mm to about 8 mm, about 5 mm to about 9 mm, about 5 mm to about 1 cm, about 5 mm to about 2 cm, about 5 mm to about 3 cm, about 5 mm to about 4 cm, about 5 mm to about 5 cm, about 5 mm to about 6 cm, about 1 cm to about 2 cm, about 1 cm to about 3 cm, about 1 cm to about 4 cm, about 1 cm to about 5 cm, about 1 cm to about 6 cm, about 2 cm to about 3 cm, about 2 cm to about 4 cm, about 2 cm to about 5 cm, about 2 cm to about 6 cm, about 3 cm to about 4 cm, about 3 cm to about 5 cm, about 3 cm to about 6 cm, about 4 cm to about 5 cm, about 4 cm to about 6 cm, about 5 cm to about 6 cm.

In some embodiments, a tab disclosed herein can have a length that extends past the attachment location of left and right mandibular osteocutaneous ligaments. In some embodiments, a tab disclosed herein can have a length that extends, e.g., about 1 cm, about 1.5 cm, about 2 cm, about 2.5 cm, about 3 cm, about 3.5 cm, or about 4 cm past the attachment location of the left and right mandibular osteocutaneous ligaments. In some embodiments, a tab disclosed herein can have a length that extends, e.g., at least 1 cm, at least 1.5 cm, at least 2 cm, at least 2.5 cm, at least 3 cm, at least 3.5 cm, or at least 4 cm past the attachment location of the left and right mandibular osteocutaneous ligaments. In some embodiments, a tab disclosed herein can have a length that extends, e.g., at most 1 cm, at most 1.5 cm, at most 2 cm, at most 2.5 cm, at most 3 cm, at most 3.5 cm, or at most 4 cm past the attachment location of the left and right mandibular osteocutaneous ligaments. In some embodiments, a tab disclosed herein can have a length that extends, e.g., about 1 cm to about 1.5 cm, about 1 cm to about 2 cm, about 1 cm to about 2.5 cm, about 1 cm to about 3 cm, about 1 cm to about 3.5 cm, about 1 cm to about 4 cm, about 2 cm to about 3 cm, bout 2 cm to about 3.5 cm, about 2 cm to about 4 cm, about 3 cm to about 3.5 cm, about 3 cm to about 4 cm, or about 3.5 cm to about 4 cm, past the attachment location of the left and right mandibular osteocutaneous ligaments. In some embodiments, a tab disclosed herein can have a length that extend all the way to the gonial angle of the mandible.

In some embodiments, a tab disclosed herein can have a height of, e.g., about 1 mm, about 2 mm, about 2.5 mm, about 3 mm, about 4 mm, about 4.5 mm, or about 5 mm. In some embodiments, a tab disclosed herein can have a height of, e.g., at least 1 mm, at least 2 mm, at least 2.5 mm, at least 3 mm, at least 4 mm, at least 4.5 mm, or at least 5 mm. In some embodiments, a tab disclosed herein can have a height of, e.g., at most 1 mm, at most 2 mm, at most 2.5 mm, at most 3 mm, or at most 4 mm, at most 4.5 mm, or at most 5 mm. In some embodiments, a tab disclosed herein can have a height of, e.g., about 1 mm to about 2 mm, about 1 mm to about 2.5 mm, about 1 mm to about 1 mm, about 1 mm to about 3.5 mm, about 1 mm to about 4 mm, about 1 mm to about 4.5 mm, about 1 mm to about 5 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3.5 mm to about 4 mm, about 3 mm to about 4.5 mm, about 3.5 mm to about 5 mm, or about 4 mm to about 5 mm.

In some embodiments, a tab disclosed herein can have a thickness of, e.g., about 1 mm, about 2 mm, about 2.5 mm, about 3 mm, about 4 mm, about 4.5 mm, or about 5 mm. In some embodiments, a tab disclosed herein can have a thickness of, e.g., at least 1 mm, at least 2 mm, at least 2.5 mm, at least 3 mm, at least 4 mm, at least 4.5 mm, or at least 5 mm. In some embodiments, a tab disclosed herein can have a thickness of, e.g., at most 1 mm, at most 2 mm, at most 2.5 mm, at most 3 mm, or at most 4 mm, at most 4.5 mm, or at most 5 mm. In some embodiments, a tab disclosed herein can have a thickness of, e.g., about 1 mm to about 2 mm, about 1 mm to about 2.5 mm, about 1 mm to about 1 mm, about 1 mm to about 3.5 mm, about 1 mm to about 4 mm, about 1 mm to about 4.5 mm, about 1 mm to about 5 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3.5 mm to about 4 mm, about 3 mm to about 4.5 mm, about 3.5 mm to about 4 mm, about 3 mm to about 4.5 mm, about 3.5 mm to about 5 mm, or about 4 mm to about 5 mm.

Aspects of the present specification can also be described by the following embodiments:

1. A method of mandibular augmentation or enhancement, comprising: accessing one or more segments of a left and/or a right anterior mental fibrous condensation; releasing one or more segments of the left and/or the right anterior mental fibrous condensation from their one or more respective mandibular attachment sites; subperiosteally releasing one or more mandibular ligaments from their respective one or more mandibular attachment points to form a subperiosteal implantation cavity; and inserting of a mandibular implant into the subperiosteal implantation cavity.
2. The method of embodiment 1, wherein accessing the one or more segments of a left and/or right anterior mental fibrous condensation is accomplished by creating an incision through an external skin surface located in a submental space.
3. The method of embodiment 2, further comprising dissecting through soft tissue underlying the incision site until one or more attachment points of one or more segments of a left and/or a right anterior mental fibrous condensation are identified.
4. The method of any one of embodiments 1-3, wherein accessing the one or more segments of a left and/or right anterior mental fibrous condensation is accomplished by creating an intraoral incision through the vestibule of the mouth.
5. The method of embodiment 4, further comprising dissecting deep through the soft tissue underlying the incision site to a sub-periosteal level and then extending the dissection until one or more attachment points of one or more segments of a left and/or a right anterior mental fibrous condensation are identified.
6. The method of any one of embodiments 1-5, wherein releasing is accomplished by excising and severing the one or more segments at their respective attachment sites on the mandible using a scalpel, a scissors, or an electromagnetic energy device.
7. The method of any one of embodiments 1-6, wherein the one or more mandibular ligaments comprises a left medial mandibular ligament, a left mandibulocutaneous ligament, a right medial mandibular ligament, a right mandibulocutaneous ligament, or any combination thereof.
8. The method of any one of embodiments 1-7, wherein subperiosteally releasing one or more mandibular ligaments is accomplished by blunt dissection using a periosteal elevator.
9. The method of any one of embodiments 1-8, the subperiosteal implantation cavity is extended laterally any posterior distance past an attachment site of the one or more mandibular ligaments.
10. The method of any one of embodiments 1-9, wherein the subperiosteal implantation cavity formed extends laterally to a point posterior to an attachment site of a mandibulocutaneous ligament.
11. The method of any one of embodiments 1-10, wherein the subperiosteal implantation cavity formed extends laterally to a point posterior to past an attachment site of a mandibulocutaneous ligament and up to a gonial angle.
12. The method of any one of embodiments 1-11, wherein the subperiosteal implantation cavity formed extends about midway between an attachment site of a mandibulocutaneous ligament and a gonial angle.
13. The method of any one of embodiments 1-12, wherein the subperiosteal implantation cavity formed extends to a gonial angle.
14. The method of any one of embodiments 1-13, further comprising closing of the incision site once insertion of the mandibular implant is completed.
15. The method of any one of embodiments 1-14, wherein after insertion the mandibular implant acts as a spacer to maintain periosteum above the mandible and inhibit periosteal re-attachment.
16. The method of any one of embodiments 1-15, wherein after insertion of the mandibular implant a chin area is augmented by a volume that is at least about 20% more than the volume of the mandibular implant.
17. The method of any one of embodiments 1-16, wherein the inserted mandibular implant augments a jaw area from an attachment site of a left mandibulocutaneous ligament to an attachment site of a right mandibulocutaneous ligament.
18. The method of any one of embodiments 1-16, wherein the inserted mandibular implant augments a jaw area from a point posterior to an attachment site of a left mandibulocutaneous ligament and up to a left gonial angle to a point posterior to an attachment site of a right mandibulocutaneous ligament and up to a right gonial angle.
19. The method of any one of embodiments 1-16, wherein the inserted mandibular implant augments a jaw area from about midway between an attachment site of a left mandibulocutaneous ligament and a left gonial angle to about midway between an attachment site of a right mandibulocutaneous ligament and a right gonial angle.
20. The method of any one of embodiments 1-16, wherein the inserted mandibular implant augments a jaw area from a left gonial angle to a right gonial angle.
21. The method of any one of embodiments 1-20, wherein the mandibular implant comprises a volume of about 1 mL and about 50 mL.
22. The method of any one of embodiments 1-21, wherein the method reduces or eliminates jowls.
23. The method of any one of embodiments 1-21, wherein the method lifts the jowls.
24. The method of any one of embodiments 1-23, wherein the method does not comprise performing a face lift.
25. The method of any one of embodiments 1-23, further comprising performing a face lift procedure.
26. The method of any one of embodiments 1-25, further comprising augmenting a facial feature with one or more dermal filler materials.
27. A mandibular implant comprising: a body having a substantially U-shaped structure comprising a first end region and a second end region, the body sized and dimensioned to an axial length configured to extend from a point laying in a region between an attachment location of a left mandibular osteocutaneous ligament and a left gonial angle to a region between the attachment location of the right mandibular osteocutaneous ligament and the right gonial angle.

28. The mandibular implant of embodiment 27, wherein the axial length extends past the attachment location of the left mandibular osteocutaneous ligament by about 3 mm to about 5 cm and extends past the attachment location of the right mandibular osteocutaneous ligament by about 3 mm to about 5 cm.
29. The mandibular implant of embodiment 27, wherein the axial length extends to the left gonial angle and to the right gonial angle.
30. The mandibular implant of any one of embodiments 27-29, wherein the body comprising a mental arch, a left lateral arm, and a right lateral arm.
31. The mandibular implant of any one of embodiments 27-30, wherein the body further comprises one or more protrusions projecting radially outward from an outer surface of the body.
32. The mandibular implant of any one of embodiments 27-31, wherein the body further comprises a ramus extension projecting superiorly from a top edge of the first end region of the body and a ramus extension projecting superiorly from a top edge of the second end region of the body.
33. The mandibular implant of any one of embodiments 27-32, wherein the body further comprises one or more tabs projecting posteriorly from an inner surface of the body.
34. The mandibular implant of embodiment 33, wherein the one or more tabs comprise a base tab, a submental tab, an extended tab, or any combination thereof.
35. The mandibular implant of any one of embodiments 27-34, wherein an outer surface and an inner surface of the body, the outer surface being smooth, the inner surface being smooth, or both the outer and inner surfaces being smooth.
36. The mandibular implant of any one of embodiments 27-35, wherein the body comprises an outer surface and an inner surface, the outer surface being textured, the inner surface being textured, or both the outer and inner surfaces being textured.
37. The mandibular implant of any one of embodiments 27-36, wherein the body is flexible.
38. The mandibular implant of any one of embodiments 27-37, wherein the body is composed of implantable biomaterial.
39. The method of embodiment 37, wherein the implantable biomaterial comprises silicone.
40. The mandibular implant of any one of embodiments 27-39, wherein the body comprises an outer shell and an inner core.
41. The mandibular implant of embodiment 40, wherein the shell has one unitary layer or a plurality of layers.
42. The mandibular implant of any one of embodiments 27-41, wherein the body is configured to be substantially filled with a filler.
43. A mandibular implant as defined in any one of claims 27-41 for use in the augmentation or enhancement of a jaw of an individual.
44. The mandibular implant of claim 43, wherein the mandibular implant augments a jaw area from a point posterior to an attachment site of a left mandibulocutaneous ligament to a point posterior to an attachment site of a right mandibulocutaneous ligament.
45. The mandibular implant of claim 43, wherein the mandibular implant augments a jaw area from a point posterior to an attachment site of a left mandibulocutaneous ligament and up to a left gonial angle to a point posterior to an attachment site of a right mandibulocutaneous ligament and up to a right gonial angle.
46. The mandibular implant of claim 43, wherein the mandibular implant augments a jaw area from about midway between an attachment site of a left mandibulocutaneous ligament and a left gonial angle to about midway between an attachment site of a right mandibulocutaneous ligament and a right gonial angle.
47. The mandibular implant of claim 43, wherein the mandibular implant augments a jaw area from a left gonial angle to a right gonial angle.
48. Use of a mandibular implant as defined in any one of claims 27-41 in the augmentation or enhancement of a jaw of an individual.
49. The use of claim 48, wherein the mandibular implant augments a jaw area from a point posterior to an attachment site of a left mandibulocutaneous ligament to a point posterior to an attachment site of a right mandibulocutaneous ligament.
50. The use of claim 48, wherein the mandibular implant augments a jaw area from a point posterior to an attachment site of a left mandibulocutaneous ligament and up to a left gonial angle to a point posterior to an attachment site of a right mandibulocutaneous ligament and up to a right gonial angle.
51. The use of claim 48, wherein the mandibular implant augments a jaw area from about midway between an attachment site of a left mandibulocutaneous ligament and a left gonial angle to about midway between an attachment site of a right mandibulocutaneous ligament and a right gonial angle.
52. The use of claim 48, wherein the mandibular implant augments a jaw area from a left gonial angle to a right gonial angle.

Examples

The following non-limiting examples are provided for illustrative purposes only in order to facilitate a more complete understanding of representative embodiments now contemplated. These examples should not be construed to limit any of the embodiments described in the present specification, including those pertaining to the mandibular implants disclosed herein, the use of such disclosed implants, or the methods of mandibular augmentation or enhancement disclosed herein.

FIGS. 5A-D shows an exemplary single-piece mandibular implant 500 shaped to conform along a region of the mental protuberance and left and right mental tubercles (chin) and the entire bottom portion of the body of the mandible (side of jawline). Mandibular implant 500 is configured to augment tissue from the end of the left back jaw to the end of the right back jaw of an individual. Mandibular implant 500 comprises a mental arch 510, a left lateral arm 520 and right lateral arm 530 (please note that the dashed line demarcate mental arch 510 from each of left and right lateral arms 520, 530. Mental arch 510 comprises an outer surface 512 and inner surface 514, a top 516 and a bottom 518. Mental arch 510 is sized and dimensioned to conform to the general shape of a region of the mental protuberance and left and right mental tubercles (chin) and inner surface 514 of mental arch 510 is configured to properly seat on the top surface of a region of the mental protuberance and left and right mental tubercles. Left lateral arm 520 comprises an outer surface 522 and inner surface 524, a top 526 and a bottom 528. Similarly, right lateral arm 530 comprises an outer surface 532 and inner surface 534, a top 536 and a bottom 538. Left and right lateral arms 520, 530 are each is sized and dimensioned to conform to the general shape of the bottom portion of the body of the mandible. Additionally, inner surface 524 of left lateral arm 520 and inner surface 534 of right lateral arm 530 are each configured to properly seat on the top surface of their respective bottom portion of the mandibular body. Left and right lateral arms 520, 530 have a length that extends to the gonial angle of the mandible. The size and dimension of left and right lateral arms 520, 530 is shaped to impart a narrow jawline enhancement, with the length of each arm gradually tapering in height and thickness, each arm being about 2 mm to 3 mm high and about 1 mm to 2 mm in thickness.

FIGS. 6A-D shows an exemplary single-piece mandibular implant 600 shaped to conform along the a region of the mental protuberance and left and right mental tubercles (chin) and a section of a bottom portion of the body of the mandible (side of jawline). As such, mandibular implant 600 is configured to augment tissue from a point laying midway between the attachment location of the left mandibular osteocutaneous ligament and left back jaw to a point laying midway between the attachment location of the right mandibular osteocutaneous ligament and the right back jaw of an individual. Mandibular implant 600 comprises a mental arch 610, a left lateral arm 620 and right lateral arm 630 (please note that the dashed line demarcate mental arch 610 from each of left and right lateral arms 620, 630. Mental arch 610 comprises an outer surface 612 and inner surface 614, a top 616 and a bottom 618. Mental arch 610 is sized and dimensioned to conform to the general shape of a region of the mental protuberance and left and right mental tubercles and inner surface 614 of mental arch 610 is configured to properly seat on the top surface of a region of the mental protuberance and left and right mental tubercles. Left lateral arm 620 comprises an outer surface 622 and inner surface 624, a top 626 and a bottom 628. Similarly, right lateral arm 630 comprises an outer surface 632 and inner surface 634, a top 636 and a bottom 638. Left and right lateral arms 620, 630 are each is sized and dimensioned to conform to the general shape of the bottom portion of the body of the mandible. Additionally, inner surface 624 of left lateral arm 620 and inner surface 634 of right lateral arm 630 are each configured to properly seat on the top surface of their respective bottom portion of the mandibular body. Left and right lateral arms 620, 630 have a length that extends along the jawline to midway between the attachment location of the mandibular osteocutaneous ligament and the gonial angle of the mandible. The size and dimension of left and right lateral arms 520, 530 is shaped to impart a full jawline enhancement, with the length of each arm gradually tapering in height and thickness, each arm being about 3 mm to 5 mm high and about 2 mm to 3.5 mm in thickness.

FIGS. 7A-D shows an exemplary single-piece mandibular implant 700 shaped to conform along a region of the mental protuberance and left and right mental tubercles (chin) and the entire bottom portion of the body of the mandible (side of jawline). Mandibular implant 700 is configured to augment tissue from the end of the left back jaw to the end of the right back jaw of an individual. Mandibular implant 700 comprises a mental arch 710, a left lateral arm 720 and right lateral arm 730 (please note that the dashed line demarcate mental arch 710 from each of left and right lateral arms 720, 730. Mental arch 710 comprises an outer surface 712 and inner surface 714, a top 716 and a bottom 718. Mental arch 710 is sized and dimensioned to conform to the general shape of a region of the mental protuberance and left and right mental tubercles and inner surface 714 of mental arch 710 is configured to properly seat on the top surface of a region of the mental protuberance and left and right mental tubercles. Left lateral arm 720 comprises an outer surface 722 and inner surface 724, a top 726 and a bottom 728. Similarly, right lateral arm 730 comprises an outer surface 732 and inner surface 734, a top 736 and a bottom 738. Left and right lateral arms 720, 730 are each is sized and dimensioned to conform to the general shape of the bottom portion of the body of the mandible. Additionally, inner surface 724 of left lateral arm 720 and inner surface 734 of right lateral arm 730 are each configured to properly seat on the top surface of their respective bottom portion of the mandibular body. Left and right lateral arms 720, 730 have a length that extends to the gonial angle of the mandible. The size and dimension of left and right lateral arms 720, 730 is shaped to impart a full jawline enhancement, with the length of each arm gradually tapering in height and thickness, each arm being about 3 mm to 5 mm high and about 2 mm to 3.5 mm in thickness. Additionally, left and right lateral arms 720, 730 each comprise a protrusion 740 position on an outer surface 724, 734 of left and right lateral arms 720, 730 respectively. Protrusions 740 are each sized and dimensioned identically or substantially similar to each other, are symmetrically positioned on left and right lateral arms 720, 730 and are configured to fill in and smooth out soft tissue defects on the side of the jaw and provide an aesthetic enhancement to the jawline.

FIGS. 8A-D shows an exemplary single-piece mandibular implant 800 shaped to conform along a region of the mental protuberance and left and right mental tubercles (chin) and the entire bottom portion of the body of the mandible (side of jawline). Mandibular implant 800 is configured to augment tissue from the end of the left back jaw to the end of the right back jaw of an individual. Mandibular implant 700 comprises a mental arch 810, a left lateral arm 820 and right lateral arm 830 (please note that the dashed line demarcate mental arch 810 from each of left and right lateral arms 820, 830. Mental arch 810 comprises an outer surface 812 and inner surface 814, a top 816 and a bottom 818. Mental arch 810 is sized and dimensioned to conform to the general shape of a region of the mental protuberance and left and right mental tubercles and inner surface 814 of mental arch 810 is configured to properly seat on the top surface of a region of the mental protuberance and left and right mental tubercles. Left lateral arm 820 comprises an outer surface 822 and inner surface 824, a top 826 and a bottom 828. Similarly, right lateral arm 830 comprises an outer surface 832 and inner surface 834, a top 836 and a bottom 838. Left and right lateral arms 820, 830 are each is sized and dimensioned to conform to the general shape of the bottom portion of the body of the mandible. Additionally, inner surface 824 of left lateral arm 820 and inner surface 834 of right lateral arm 830 are each configured to properly seat on the top surface of their respective bottom portion of the mandibular body. Left and right lateral arms 820, 830 have a length that extends to the gonial angle of the mandible. The size and dimension of left and right lateral arms 820, 830 is shaped to impart a narrow jawline enhancement, with the length of each arm gradually tapering in height and thickness, each arm being about 2 mm to 3 mm high and about 1 mm to 2 mm in thickness. Additionally, left and right lateral arms 820, 830 each comprise a protrusion 840 position on an outer surface 824, 834 of left and right lateral arms 820, 830 respectively. Protrusions 840 are each sized and dimensioned identically or substantially similar to each other, are symmetrically positioned on left and right lateral arms 820, 830 and are configured to fill in and smooth out soft tissue defects on the side of the jaw and provide an aesthetic enhancement to the jawline.

FIGS. 9A-D shows an exemplary single-piece mandibular implant 900 shaped to conform along a region of the mental protuberance and left and right mental tubercles (chin) and the entire bottom portion of the body of the mandible (side of jawline). Mandibular implant 900 is configured to augment tissue from the end of the left back jaw to the end of the right back jaw of an individual. Mandibular implant 900 comprises a mental arch 910, a left lateral arm 920 and right lateral arm 930 (please note that the dashed line demarcate mental arch 910 from each of left and right lateral arms 920, 930. Mental arch 910 comprises an outer surface 912 and inner surface 914, a top 916 and a bottom 918. Mental arch 910 is sized and dimensioned to conform to the general shape of a region of the mental protuberance and left and right mental tubercles and inner surface 914 of mental arch 910 is configured to properly seat on the top surface of a region of the mental protuberance and left and right mental tubercles. Left lateral arm 920 comprises an outer surface 922 and inner surface 924, a top 926 and a bottom 928. Similarly, right lateral arm 930 comprises an outer surface 932 and inner surface 934, a top 936 and a bottom 938. Left and right lateral arms 920, 930 are each is sized and dimensioned to conform to the general shape of the bottom portion of the body of the mandible. Additionally, inner surface 924 of left lateral arm 920 and inner surface 934 of right lateral arm 930 are each configured to properly seat on the top surface of their respective bottom portion of the mandibular body. Left and right lateral arms 920, 930 have a length that extends to the gonial angle of the mandible. The size and dimension of left and right lateral arms 920, 930 is shaped to impart a full jawline enhancement, with the length of each arm being about 3 mm to 5 mm high and about 2 mm to 3.5 mm in thickness. Additionally, left and right lateral arms 920, 930 each comprise a ramus extension 950 at their respective lateral ends. Each ramus extension 950 is an expansion from top 926 of left lateral arm 920 or top 936 of right lateral arm 930 to form a discrete back jaw component (mandibular angle augmentation). Ramus extensions 950 are each is sized and dimensioned to conform to the general shape of a portion of the ramus of the mandible. Additionally, an inner surface 952 of each ramus extension 950 is configured to properly seat on the top surface of their respective portion of the ramus. Ramus extensions 950 are each sized and dimensioned identically or substantially similar to each other and are designed to provide an aesthetic enhancement to the jaw.

FIGS. 10A-D shows an exemplary single-piece mandibular implant 1000 shaped to conform along a region of the mental protuberance and left and right mental tubercles (chin) and the entire bottom portion of the body of the mandible (side of jawline). Mandibular implant 1000 is configured to augment tissue from the end of the left back jaw to the end of the right back jaw of an individual. Mandibular implant 1000 comprises a mental arch 1010, a left lateral arm 1020 and right lateral arm 1030 (please note that the dashed line demarcate mental arch 1010 from each of left and right lateral arms 1020, 1030. Mental arch 1010 comprises an outer surface 1012 and inner surface 1014, a top 1016 and a bottom 1018. Mental arch 1010 is sized and dimensioned to conform to the general shape of a region of the mental protuberance and left and right mental tubercles and inner surface 1014 of mental arch 1010 is configured to properly seat on the top surface of a region of the mental protuberance and left and right mental tubercles. Left lateral arm 1020 comprises an outer surface 1022 and inner surface 1024, a top 1026 and a bottom 1028. Similarly, right lateral arm 1030 comprises an outer surface 1032 and inner surface 1034, a top 1036 and a bottom 1038. Left and right lateral arms 1020, 1030 are each is sized and dimensioned to conform to the general shape of the bottom portion of the body of the mandible. Additionally, inner surface 1024 of left lateral arm 1020 and inner surface 1034 of right lateral arm 1030 are each configured to properly seat on the top surface of their respective bottom portion of the mandibular body. Left and right lateral arms 1020, 1030 have a length that extends to the gonial angle of the mandible. The size and dimension of left and right lateral arms 1020, 1030 is shaped to impart a full jawline enhancement, with the length of each arm being about 3 mm to 5 mm high and about 2 mm to 3.5 mm in thickness. Additionally, left and right lateral arms 1020, 1030 each comprise a ramus extension 1050 at their respective lateral ends. Each ramus extension 1050 is an expansion from top 1026 of left lateral arm 1020 or top 1036 of right lateral arm 1030 to form a discrete back jaw component (mandibular angle augmentation). Ramus extensions 1050 are each is sized and dimensioned to conform to the general shape of a portion of the ramus of the mandible. Additionally, an inner surface 1052 of each ramus extension 1050 is configured to properly seat on the top surface of their respective portion of the ramus. Ramus extensions 1050 are each sized and dimensioned identically or substantially similar to each other and are designed to provide an aesthetic enhancement to the jaw. Left and right lateral arms 1020, 1030 also each comprise a protrusion 1040 position on an outer surface 1024, 1034 of left and right lateral arms 1020, 1030 respectively. Protrusions 1040 are each sized and dimensioned identically or substantially similar to each other, are symmetrically positioned on left and right lateral arms 1020, 1030 and are configured to fill in and smooth out soft tissue defects on the side of the jaw and provide an aesthetic enhancement to the jawline.

FIGS. 11A-D shows an exemplary single-piece mandibular implant 1100 shaped to conform along a region of the mental protuberance and left and right mental tubercles (chin) and the entire bottom portion of the body of the mandible (side of jawline). Mandibular implant 1100 is configured to augment tissue from the end of the left back jaw to the end of the right back jaw of an individual. Mandibular implant 1100 comprises a mental arch 1110, a left lateral arm 1120 and right lateral arm 1130 (please note that the dashed line demarcate mental arch 1110 from each of left and right lateral arms 1120, 1130. Mental arch 1110 comprises an outer surface 1112 and inner surface 1114, a top 1116 and a bottom 1118. Mental arch 1110 is sized and dimensioned to conform to the general shape of a region of the mental protuberance and left and right mental tubercles and inner surface 1114 of mental arch 1110 is configured to properly seat on the top surface of a region of the mental protuberance and left and right mental tubercles. Left lateral arm 1120 comprises an outer surface 1122 and inner surface 1124, a top 1126 and a bottom 1128. Similarly, right lateral arm 1130 comprises an outer surface 1132 and inner surface 1134, a top 1136 and a bottom 1138. Left and right lateral arms 1120, 1130 are each is sized and dimensioned to conform to the general shape of the bottom portion of the body of the mandible. Additionally, inner surface 1124 of left lateral arm 1120 and inner surface 1134 of right lateral arm 1130 are each configured to properly seat on the top surface of their respective bottom portion of the mandibular body. Left and right lateral arms 1120, 1130 have a length that extends to the gonial angle of the mandible. The size and dimension of left and right lateral arms 1120, 1130 is shaped to impart a full jawline enhancement, with the length of each arm gradually tapering in height and thickness, each arm being about 3 mm to 5 mm high and about 2 mm to 3.5 mm in thickness. Additionally, left and right lateral arms 1120, 1130 each comprise a base tab 1160 position on bottom 1128 of inner surface 1122, 1132 of left and right lateral arms 1120, 1130 respectively. Base tabs 1160 are laterally-spaced apart and is configured to fit underneath the edge of the left and right portions of the base of the mandibular body in order to secure proper placement of mandibular implant 1100. Base tabs 1160 increase stability of mandibular implant 1100, prevent fibrous attachment to the mandible, as well as provide a smooth transition between different or adjacent areas of the mandible.

FIGS. 12A-D shows an exemplary single-piece mandibular implant 1200 shaped to conform along a region of the mental protuberance and left and right mental tubercles (chin) and the entire bottom portion of the body of the mandible (side of jawline). Mandibular implant 1200 is configured to augment tissue from the end of the left back jaw to the end of the right back jaw of an individual. Mandibular implant 1200 comprises a mental arch 1210, a left lateral arm 1220 and right lateral arm 1230 (please note that the dashed line demarcate mental arch 1210 from each of left and right lateral arms 1220, 1230. Mental arch 1210 comprises an outer surface 1212 and inner surface 1214, a top 1216 and a bottom 1218. Mental arch 1210 is sized and dimensioned to conform to the general shape of a region of the mental protuberance and left and right mental tubercles and inner surface 1214 of mental arch 1210 is configured to properly seat on the top surface of a region of the mental protuberance and left and right mental tubercles. Left lateral arm 1220 comprises an outer surface 1222 and inner surface 1224, a top 1226 and a bottom 1228. Similarly, right lateral arm 1230 comprises an outer surface 1232 and inner surface 1234, a top 1236 and a bottom 1238. Left and right lateral arms 1220, 1230 are each is sized and dimensioned to conform to the general shape of the bottom portion of the body of the mandible. Additionally, inner surface 1224 of left lateral arm 1220 and inner surface 1234 of right lateral arm 1230 are each configured to properly seat on the top surface of their respective bottom portion of the mandibular body. Left and right lateral arms 1220, 1230 have a length that extends to the gonial angle of the mandible. The size and dimension of left and right lateral arms 1220, 1230 is shaped to impart a full jawline enhancement, with the length of each arm gradually tapering in height and thickness, each arm being about 3 mm to 5 mm high and about 2 mm to 3.5 mm in thickness. Additionally, mental arch 1210 comprises a submental tab 1270 position on bottom 1228 of inner surface 1212 of mental arch 1210. Submental tab 1270 is configured to fit underneath the edge of the left and right mental protuberances in order to secure proper placement of mandibular implant 1200. Submental tab 1270 increases stability of mandibular implant 1200, prevent fibrous attachment to the mandible, as well as provide a smooth transition between different or adjacent areas of the mandible.

FIGS. 13A-D shows an exemplary single-piece mandibular implant 1300 shaped to conform along a region of the mental protuberance and left and right mental tubercles (chin) and the entire bottom portion of the body of the mandible (side of jawline). Mandibular implant 1300 is configured to augment tissue from the end of the left back jaw to the end of the right back jaw of an individual. Mandibular implant 1300 comprises a mental arch 1310, a left lateral arm 1320 and right lateral arm 1330 (please note that the dashed line demarcate mental arch 1310 from each of left and right lateral arms 1320, 1330. Mental arch 1310 comprises an outer surface 1312 and inner surface 1314, a top 1316 and a bottom 1318. Mental arch 1310 is sized and dimensioned to conform to the general shape of a region of the mental protuberance and left and right mental tubercles and inner surface 1314 of mental arch 1310 is configured to properly seat on the top surface of a region of the mental protuberance and left and right mental tubercles. Left lateral arm 1320 comprises an outer surface 1322 and inner surface 1324, a top 1326 and a bottom 1328. Similarly, right lateral arm 1330 comprises an outer surface 1332 and inner surface 1334, a top 1336 and a bottom 1338. Left and right lateral arms 1320, 1330 are each is sized and dimensioned to conform to the general shape of the bottom portion of the body of the mandible. Additionally, inner surface 1324 of left lateral arm 1320 and inner surface 1334 of right lateral arm 1330 are each configured to properly seat on the top surface of their respective bottom portion of the mandibular body. Left and right lateral arms 1320, 1330 have a length that extends to the gonial angle of the mandible. The size and dimension of left and right lateral arms 1320, 1330 is shaped to impart a full jawline enhancement, with the length of each arm gradually tapering in height and thickness, each arm being about 3 mm to 5 mm high and about 2 mm to 3.5 mm in thickness. Additionally, mandibular implant 1300 comprises base tabs 1360 on left and right lateral arms 1320, 1330 position on bottom 1328 of inner surface 1322, 1332 of left and right lateral arms 1320, 1330 respectively as well as submental tab 1370 position on bottom 1328 of inner surface 1312 of mental arch 1310

FIGS. 14A-D shows an exemplary single-piece mandibular implant 1400 shaped to conform along a region of the mental protuberance and left and right mental tubercles (chin) and the entire bottom portion of the body of the mandible (side of jawline). Mandibular implant 1400 is configured to augment tissue from the end of the left back jaw to the end of the right back jaw of an individual. Mandibular implant 1400 comprises a mental arch 1410, a left lateral arm 1420 and right lateral arm 1430 (please note that the dashed line demarcate mental arch 1410 from each of left and right lateral arms 1420, 1430. Mental arch 1410 comprises an outer surface 1412 and inner surface 1414, a top 1416 and a bottom 1418. Mental arch 1410 is sized and dimensioned to conform to the general shape of a region of the mental protuberance and left and right mental tubercles and inner surface 1414 of mental arch 1410 is configured to properly seat on the top surface of a region of the mental protuberance and left and right mental tubercles. Left lateral arm 1420 comprises an outer surface 1422 and inner surface 1424, a top 1426 and a bottom 1428. Similarly, right lateral arm 1430 comprises an outer surface 1432 and inner surface 1434, a top 1436 and a bottom 1438. Left and right lateral arms 1420, 1430 are each is sized and dimensioned to conform to the general shape of the bottom portion of the body of the mandible. Additionally, inner surface 1424 of left lateral arm 1420 and inner surface 1434 of right lateral arm 1430 are each configured to properly seat on the top surface of their respective bottom portion of the mandibular body. Left and right lateral arms 1420, 1430 have a length that extends to the gonial angle of the mandible. The size and dimension of left and right lateral arms 1420, 1430 is shaped to impart a full jawline enhancement, with the length of each arm gradually tapering in height and thickness, each arm being about 3 mm to 5 mm high and about 2 mm to 3.5 mm in thickness. Additionally, mental arch 1410 comprises an extended tab 1480 position on bottom 1428 of inner surface 1412 of mental arch 1410 and bottom 1428 of inner surface 1422, 1432 of left and right lateral arms 1420, 1430. Extended tab 1480 is configured to fit underneath the edge of the left and right mental protuberances and underneath the edge of the left and right portions of the base of the mandibular body in order to secure proper placement of mandibular implant 1400. Extended tab 1480 increases stability of mandibular implant 1400, prevent fibrous attachment to the mandible, as well as provide a smooth transition between different or adjacent areas of the mandible.

Figure 15:
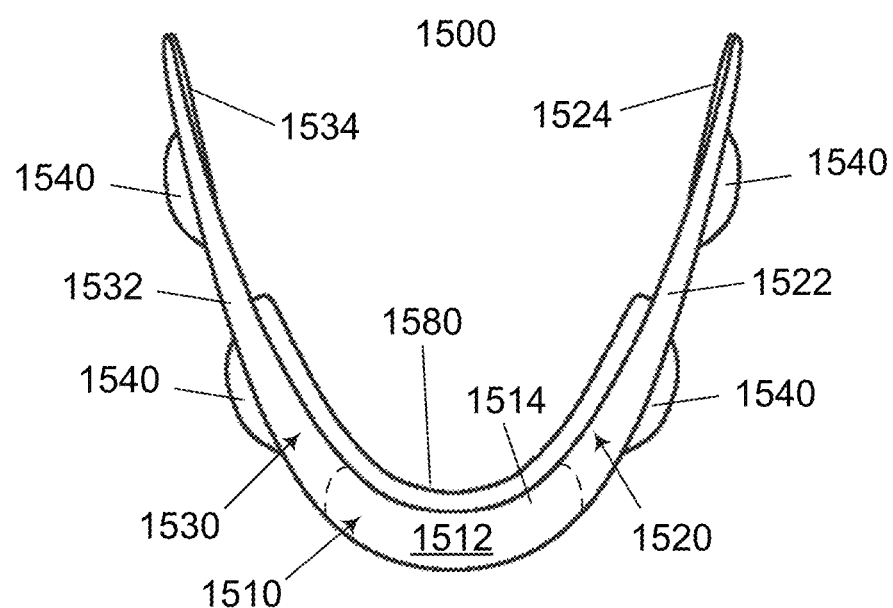
FIG. 15 is a top plan view of a single-piece mandibular implant disclosed herein comprising a mental arch and full left and right lateral arms with each arm with each arm comprising two protrusions and being configured to extend along the jawline to its respective gonial angle and the implant comprising an extended tab on the inner surface of the mental arch which extends into a portion of each arm.

FIG. 15 shows an exemplary single-piece mandibular implant 1500 shaped to conform along a region of the mental protuberance and left and right mental tubercles (chin) and the entire bottom portion of the body of the mandible (side of jawline). Mandibular implant 1500 is configured to augment tissue from the end of the left back jaw to the end of the right back jaw of an individual. Mandibular implant 1400 comprises a mental arch 1510, a left lateral arm 1520 and right lateral arm 1530 (please note that the dashed line demarcate mental arch 1510 from each of left and right lateral arms 1420, 1530. Mental arch 1510 comprises an outer surface 1512 and inner surface 1514, a top 1516 and a bottom 1518. Mental arch 1510 is sized and dimensioned to conform to the general shape of a region of the mental protuberance and left and right mental tubercles and inner surface 1514 of mental arch 1510 is configured to properly seat on the top surface of a region of the mental protuberance and left and right mental tubercles. Left lateral arm 1520 comprises an outer surface 1522 and inner surface 1524, a top 1526 and a bottom 1528. Similarly, right lateral arm 1530 comprises an outer surface 1532 and inner surface 534, a top 1536 and a bottom 1538. Left and right lateral arms 1520, 1530 are each is sized and dimensioned to conform to the general shape of the bottom portion of the body of the mandible. Additionally, inner surface 1524 of left lateral arm 1520 and inner surface 1534 of right lateral arm 1530 are each configured to properly seat on the top surface of their respective bottom portion of the mandibular body. Left and right lateral arms 1520, 1530 have a length that extends to the gonial angle of the mandible. The size and dimension of left and right lateral arms 1520, 1530 is shaped to impart a full jawline enhancement, with the length of each arm gradually tapering in height and thickness, each arm being about 3 mm to 5 mm high and about 2 mm to 3.5 mm in thickness. Additionally, mental arch 1510 comprises an extended tab 1580 position on bottom 1528 of inner surface 1512 of mental arch 1510 and bottom 1528 of inner surface 1522, 1532 of left and right lateral arms 1520, 1530. Extended tab 1580 is configured to fit underneath the edge of the left and right mental protuberances and underneath the edge of the left and right portions of the base of the mandibular body in order to secure proper placement of mandibular implant 1500. Extended tab 1580 increases stability of mandibular implant 1500, prevent fibrous attachment to the mandible, as well as provide a smooth transition between different or adjacent areas of the mandible. Left and right lateral arms 1520, 1530 also each comprise two protrusions 1540 position on an outer surface 1524, 1534 of left and right lateral arms 1520, 1530 respectively. Protrusions 1540 are each sized and dimensioned identically or substantially similar to each other, are symmetrically positioned on left and right lateral arms 1520, 1530 and are configured to fill in and smooth out soft tissue defects on the side of the jaw and provide an aesthetic enhancement to the jawline.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps and/or limitations may be made for any one of the elements, steps or limitations in a claim set forth below or that a single element, step or limitation may be substituted for two or more elements, steps and/or limitations in such a claim. Although elements, steps or limitations may be described above as acting in certain combinations and even initially claimed as such, it is to be expressly understood that one or more elements, steps and/or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above combination even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including", "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A method of mandibular augmentation or enhancement, comprising:
    accessing one or more segments of a left and/or a right anterior mental fibrous condensation;
    releasing one or more segments of the left and/or the right anterior mental fibrous condensation from their one or more respective mandibular attachment sites;
    subperiosteally releasing one or more mandibular ligaments from their respective one or more mandibular attachment points to form a subperiosteal implantation cavity; and
    inserting of a mandibular implant into the subperiosteal implantation cavity.

2. The method of claim 1, wherein the one or more mandibular ligaments comprises a left medial mandibular ligament, a left mandibulocutaneous ligament, a right medial mandibular ligament, a right mandibulocutaneous ligament, or any combination thereof.

3. The method of claim 1, wherein the subperiosteal implantation cavity formed extends laterally past a point posterior to an attachment site of a mandibulocutaneous ligament.

4. The method of claim 1, wherein the inserted mandibular implant augments a jaw area from a point posterior to an attachment site of a left mandibulocutaneous ligament to a point posterior to an attachment site of a right mandibulocutaneous ligament.

5. The method of claim 1, wherein the mandibular implant comprising: a body having a substantially U-shaped structure comprising a first end region and a second end region, the body sized and dimensioned to an axial length configured to extend from a point laying in a region between an attachment location of a left mandibular osteocutaneous ligament and a left gonial angle to a region between the attachment location of the right mandibular osteocutaneous ligament and the right gonial angle.

6. The method of claim 5, wherein the axial length extends past the attachment location of the left mandibular osteocutaneous ligament by about 3 mm to about 5 cm and extends past the attachment location of the right mandibular osteocutaneous ligament by about 3 mm to about 5 cm.

7. The method of claim 5, wherein the axial length extends to the left gonial angle and to the right gonial angle.

8. The method of claim 5, wherein the body comprising a mental arch, a left lateral arm, and a right lateral arm.

9. The method of claim 5, wherein the body further comprises one or more protrusions projecting radially outward from an outer surface of the body.

10. The method of claim 5, wherein the body further comprises a ramus extension projecting superiorly from a top edge of the first end region of the body and a ramus extension projecting superiorly from a top edge of the second end region of the body.

11. The method of claim 5, wherein the body further comprises one or more tabs projecting posteriorly from an inner surface of the body.

12. The method of claim 5, wherein the one or more tabs comprise a base tab, a submental tab, an extended tab, or any combination thereof.

13. The method of claim 5, wherein the body comprises an outer surface and an inner surface of the body, the outer surface being smooth, the inner surface being smooth, or both the outer and inner surfaces being smooth.

14. The method of claim 5, wherein the body comprises an outer surface and an inner surface, the outer surface being textured, the inner surface being textured, or both the outer and inner surfaces being textured.

15. The method of claim 5, wherein the body is flexible.

16. The method of claim 5, wherein the body is composed of implantable biomaterial.

17. The method of claim 16, wherein the implantable biomaterial comprises silicone.

18. The method of claim 5, wherein the body comprises an outer shell and an inner core.

19. The method of claim 18, wherein the outer shell has one unitary layer or a plurality of layers.

20. The method of claim 5, wherein the body is configured to be substantially filled with a filler.

* * * * *